US008389576B2

(12) United States Patent
Jalan et al.

(10) Patent No.: US 8,389,576 B2
(45) Date of Patent: Mar. 5, 2013

(54) COMPOSITIONS COMPRISING ORNITHINE AND PHENYLACETATE OR PHENYLBUTYRATE FOR TREATING HEPATIC ENCEPHALOPATHY

(75) Inventors: Rajiv Jalan, London (GB); Kamal Nayan Jalan, Kolkata (IN)

(73) Assignee: UCL Business PLC, London (GB)

( * ) Notice: Subject to any disclaimer, the term of this patent is extended or adjusted under 35 U.S.C. 154(b) by 10 days.

(21) Appl. No.: 11/720,268

(22) PCT Filed: Nov. 28, 2005

(86) PCT No.: PCT/GB2005/004539
§ 371 (c)(1),
(2), (4) Date: Oct. 3, 2007

(87) PCT Pub. No.: WO2006/056794
PCT Pub. Date: Jun. 1, 2006

(65) Prior Publication Data
US 2008/0119554 A1 May 22, 2008

(30) Foreign Application Priority Data
Nov. 26, 2004 (GB) .................................. 0426141.8
Nov. 26, 2004 (GB) .................................. 0426142.6

(51) Int. Cl.
*A01N 37/12* (2006.01)
(52) U.S. Cl. ...................................................... 514/561
(58) Field of Classification Search .................. None
See application file for complete search history.

(56) References Cited

U.S. PATENT DOCUMENTS

| 3,950,529 | A | 4/1976 | Fischer et al. |
| 4,100,293 | A | 7/1978 | Walser |
| 4,228,099 | A | 10/1980 | Walser |
| 4,284,647 | A | 8/1981 | Brusilow et al. |
| 4,320,146 | A | 3/1982 | Walser |
| 4,352,814 | A | 10/1982 | Walser |
| 4,457,942 | A | 7/1984 | Brusilow et al. |
| 5,405,761 | A | 4/1995 | Makryaleas et al. |
| 5,571,783 | A | 11/1996 | Montagne et al. |
| 5,591,613 | A | 1/1997 | Makryaleas et al. |
| 6,258,849 | B1 | 7/2001 | Burzynski |
| 6,503,530 | B1 | 1/2003 | Kang et al. |
| 6,768,024 | B1 | 7/2004 | Watson-Straughan et al. |
| 6,943,192 | B2 | 9/2005 | Burzynski |
| 2003/0195255 | A1 | 10/2003 | Summar |
| 2004/0152784 | A1 | 8/2004 | March |
| 2004/0229948 | A1* | 11/2004 | Summar et al. ............... 514/547 |
| 2005/0182064 | A1* | 8/2005 | Burzynski ..................... 514/251 |
| 2006/0045912 | A1 | 3/2006 | Truog |

FOREIGN PATENT DOCUMENTS

| CN | 1383815 | 12/2002 |
| EP | 1179347 | 2/2002 |
| EP | 1334722 | 8/2003 |
| EP | 1374863 | 1/2004 |
| EP | 1541141 | 6/2005 |
| GB | 965637 | 8/1964 |
| GB | 1067742 | 5/1967 |
| GB | 1080599 | 8/1967 |
| GB | 1310658 | 3/1973 |
| GB | 1507951 | 4/1978 |
| JP | 54-163518 A | 12/1979 |
| JP | 05221858 | 8/1993 |
| MX | PA03009902 A | 5/2005 |
| WO | WO 85/04805 | 11/1985 |
| WO | WO 97/30167 | 8/1997 |
| WO | WO-0071151 | 11/2000 |
| WO | WO-0234255 | 5/2002 |
| WO | WO-02074302 | 9/2002 |
| WO | WO 03/037378 | 5/2003 |
| WO | WO 03/045372 A1 | 6/2003 |
| WO | WO-03045372 | 6/2003 |
| WO | WO-03086074 | 10/2003 |
| WO | WO-2004019928 | 3/2004 |
| WO | WO-2005053607 | 6/2005 |
| WO | WO 2006/059237 | 6/2006 |

OTHER PUBLICATIONS

Mendenhall et al (Am J Gasteroenterol 81:540-543, 1986).*
Stedman's Medical Dictionary (27th Edition, 2002).*
Suchy et al (Liver Disease in Children, 2nd Edition, 2001, pp. 74-77).*
Briggs et al (Biochem J 160:205-209, 1976).*
Greensteine et al (Arch Biochem Biophys 64:342-354, 1956).*
Mouille et al (Am J Gasteroenterol 287:344-351, 2004).*
Riordan et al (NEJM 337:473-479, 1997).*
Berge et al (J Pharm Sci 66:1-19, 1977).*
Bleichner et al., "Frequency of infections in cirrhotic patients presenting with acute gastrointestinal haemorrhage", British Journal of Surgery, 1986, 724-726, vol. 73(9).
Chainuvati et al., "Ornicetil on encephalopathy. Effect of ornicetil (ornithine alpha-ketoglutarate) on encephalopathy in patients with acute and chronic liver disease", Acta Hepatogastroenterol (Stuttg), Dec. 1977; 434-9; vol. 24(6).
Darmaun et al., "Phenylbutyrate-induced glutamine depletion in humans: effect on leucine metabolism", Am J Physiol Endocrinol Metab, 1998, E801-E807, vol. 274.
Garden et al., "Prediction of outcome following. acute variceal haemorrhage", Br J Surg, 1985, 91-95, vol. 72.
Grace et al., "Prevention of initial variceal hemorrhage", Gastroenterology Clinics of North America, 1992; 149-161, vol. 21(1).
Herlong, et al., "The Use of Ornithine Salts of Branched-chain Ketoacids in Portal- systemic Encephalopathy," Ann Intern Med, Oct. 1980, 545-550, vol. 93(4).

(Continued)

*Primary Examiner* — Brandon Fetterolf
*Assistant Examiner* — Craig Ricci
(74) *Attorney, Agent, or Firm* — Knobbe, Martens, Olson & Bear LLP

(57) ABSTRACT

The present invention relates to use of ornithine in the manufacture of a medicament for use in combination with at least one of phenylacetate and phenylbutyrate for preventing or treating liver decompensation or hepatic encephalopathy. The invention also relates to use of at least one of phenylacetate and phenylbutyrate in the manufacture of a medicament for use in combination with ornithine for preventing or treating liver decompensation or hepatic encephalopathy.

33 Claims, 15 Drawing Sheets

OTHER PUBLICATIONS

Inoue et al., "Biochemical analysis of decreased ornithine transport activity in the liver mitochondria from patients with hyperornithinemia, hyperammonemia and homocitrullinuria", Biochim Biophys Acta, Jan. 12, 1988; 90-5; vol. 964(1).

Jeyamani et al., "Hepatitis E virus and acute-on-chronic liver failure", Indian J Gastroenterol., 2004; 45-46, vol. 23(2).

Olde Damink et al., "Decreased plasma and tissue isoleucine levels after simulated gastrointestinal bleeding by blood gavages in chronic portacaval shunted rats.", Gut, 1997; 418-424; vol. 40.

Pauwels et al., "Systemic antibiotic prophylaxis after gastrointestinal hemorrhage in cirrhotic patients with a high risk of infection", Hepatology, 1996, 802-806, vol. 24(4).

Riordan et al., "Treatment of Hepatic Encephalopathy", Current Concepts, Aug. 14, 1997, 473-479, vol. 337(7).

Teran et al., "Primary prophylaxis of variceal bleeding in cirrhosis: A cost-effectiveness analysis", Gastroenterology, 1997, 473-482, vol. 112(2).

Van Berlo et al., "Is increased ammonia liberation after bleeding in the digestive tract the consequence of complete absence of isoleucine in hemoglobin? A study in pigs.", Hepatology, Sep. 1989; 315-23; vol. 10(3).

Zieve et al., "Ammonia toxicity: Comparative protective effect of various arginine and ornithine derivatives, aspartate, benzoate, and carbamyl glutamate", Metabolic Brain Disease, 1986, 25-35, vol. 1(1).

Aggarwal et al., "Predictors of mortality and resource utilization in cirrhotic patients admitted to the medical ICU," Chest (2001) 119(5):1489-1497.

Balata et al., "Induced hyperammonemia alters neuropsychology, brain MR spectroscopy and magnetization transfer in cirrhosis," Hepatology (2003) 37(4):931-939.

Beale et al., "Early enteral supplementation with key pharmaconutrients improves sequential organ failure assessment score in critically ill patients with sepsis: outcome of a randomized, controlled, double blind trial," Crit Care Med. (2008) 36(1):131-144.

Bongers et al., "Exogenous glutamine: the clinical evidence," Crit Care Med. (2007) 35(9 Suppl):S545-S552.

Enns et al., "Survival after treatment with phenylacetate and benzoate for urea-cycle disorders," N Engl J Med. (2007) 356(22):2282-2292.

Gonzalez-Navajas et al., "Bacterial DNA in patients with cirrhosis and sterile ascites. Its role as a marker of bacterial translocation and prognostic tool," Rev Esp Enferm Dig. (2007) 99(10):599-603.

Jalan et al., "Moderate hypothermia in patients with acute liver failure and uncontrolled intracranial hypertension," Gastroenterology (2004) 127(5):1338-1346.

Kircheis et al., "Therapeutic efficacy of L-ornithine-L-aspartate infusions in patients with cirrhosis and hepatic encephalopathy: results of a placebo-controlled, double blind study," Hepatology (1997) 25(6):1351-1360.

Linderoth et al., "Short-term prognosis of community-acquired bacteremia in patients with liver cirrhosis or alcoholism: a population-based cohort study," Alcohol Clin Exp Res. (2006) 30:636-641.

Moinard et al., "Effects of ornithine 2-oxoglutarate on neutrophils in stressed rats: Evidence for the involvement of nitric oxide and polyamines," Clin Sci. (Lond)., (2002) 102(3): 287-295.

Mookerjee et al., "Neutrophil dysfunction in alcoholilc hepatitis superimposed on cirrhosis is reversible and predicts the outcome," Hepatology (2007) 46(3):831-840.

Navasa et al., "Bacterial infections in liver cirrhosis," Ital J Gastroenterol Hepatol. (1999) 31(7):616-625.

Newsholme et al., "Glutamine metabolism by lymphocytes, macrophages, and neutrophils: its importance in health and disease," J Nutr Biochem. (1999) 10(6):316-324.

Newsholme, "Why is L-glutamine metabolism important to cells of the immune system in health, postinjury, surgery or infection?" J Nutr. (2001) 131(9 Suppl): 2515S-22S.

Rajkovic et al., "Mechanisms of abnormalities in host defences against bacterial infection in liver disease," Clin Sci. (Lond.) (1985) 68(3):247-253.

Shawcross et al., "Dispelling myths in the teatment of hepatic encephalopathy," Lancet (2005) 365(9457):431-433.

Shawcross et al., "Ammonia impairs neutrophil phagocytic function in liver disease," Hepatology (2008) 48(4):1202-1212.

Sukhotnik et al., "Oral glutamine prevents gut mucosal injury and improves mucosal recovery following lipopolysaccharide endotoxemia in a rat," J Surg Res. (2007) 143(2):379-384.

Van Den Berg et al., "The effect of glutamine-enriched enteral nutrition on intestinal microflora in very low birth weight infants: a randomized controlled trial," Clin Nutr. (2007) 26(4):430-439.

Wasmuth et al., "Patients with acute on chronic liver failure display 'sepsis-like' immune paralysis," J Hepatol. (2005) 42(2):195-201.

Ytrebø et al., "Interorgan ammonia, glutamate, and glutamine trafficking in pigs with acute liver failure," Am J Physiol Gastrointest Liver Physiol. (2006) 291(3):G373-381.

Butterworth, "Pathophysiology of hepatic encephalopathy: a new look at ammonia", Metab Brain Dis., Dec. 2002; 221-7; vol. 17(4).

Database WPI, Section Ch, Week 200331, Derwent Publications Ltd., London, GB; XP002364873 & CN 1 383 815 A (LIU W) Dec. 11, 2002 abstract.

Katayama, "Ammonia metabolism and hepatic encephalopathy", Hepatology Research, 2004, S71-S78, vol. 30(1).

Ramaswamy et al., "Mouse Model for Human Arginase Deficiency", Molecular and Cellular Biology, Jul. 2002, 4491-4498, vol. 22(13).

Seiler, "Ornithine aminotransferase, a potential target for the treatment of hyperammonemias," Curr Drug Targets. Sep. 2000;1(2):119-53.

"Sodium phenylbutyrate for urea cycle enzyme deficiencies." [No authors listed] Med Lett Drugs Ther. Nov. 22, 1996;38(988):105-6.

Chainuvati, T. et al., Ornicetil on Encephalopathy: Effect of Ornicetil (Ornithine Alpha-Ketoglutarate) on Encephalopathy in Patients with Acute and Chronic Liver Disease; Acta Hepato-Gastroenterol, 1977, vol. 24, pp. 434-439, Georg Thieme Verlag Stuttgart.

Fabbri, Andrea et al., Unresponsiveness of Hepatic Nitrogen Metabolism to Glucagon Infusion in Patients with Cirrhosis: Dependence on Liver Cell Failure, Hepatology, 1993, vol. 18, No. 1, pp. 28-35, American Association for the Study of Liver Diseases.

Hamberg, Ole et al., Effects of an Increase in Protein Intake on Hepatic Efficacy for Urea Synthesis in Healthy Subjects and in Patients with Cirrhosis, Journal of Hepatology, 1992, vol. 14, pp. 237-243, Elsevier Science Publishers B.V.

Kaiser, S. et al., Ammonia and Glutamine Metabolism in Human Liver Slices: New Aspects on the Pathogenesis of Hyperammonaemia in Chronic Liver Disease, European Journal of Clinical Investigation, 1988, vol. 18, pp. 535-542.

Maier, K. P. et al., Originalien Activities of Urea-Cycle Enzymes in Chronic Liver Disease, Klinische-Wochenschrift, 1979, vol. 57, pp. 661-665, Springer-Verlag.

Meijer, Alfred J. et al., Nitrogen Metabolism and Ornithine Cycle Function, Physiological Reviews, Jul. 1990, vol. 70, No. 3, pp. 701-748, The American Physiological Society.

Rudman, Daniel, et al., Maximal Rates of Excretion and Synthesis of Urea in Normal and Cirrhotic Subjects, The Journal of Clinical Investigation, Sep. 1973, vol. 52, pp. 2241-2249.

Shangraw, Robert E. et al., Effect of Liver Disease and Transplantation on Urea Synthesis in Humans: Relationship to Acid-Base Status, Am J Physiol Gastrointest Liver Physiol, 1999, vol. 276, pp. G1145-G1152.

Vilstrup, H. et al., Elimination of Infused Amino Acids From Plasma of Control Subjects and of Patients With Cirrhosis of the Liver, European Journal of Clinical Investigation, 1982, vol. 12, pp. 197-202, Blackwell Scientific Publications.

EPO—Extended European Search Report for EP 09013613.6, dated Jan. 15, 2010.

Als-Nielsen, Bodil, et al., Non-Absorbable Disaccharides for Hepatic Encephyalopathy: Systematic Review of Randomised Trials, BMJ, 2004, p. 1-6.

Blei, Andres T., et al., Pathophysiology of Cerebral Edema in Fulminant Hepatic Failure, Journal of Hepatology, 1999, p. 771-776, vol. 31, Denmark.

Callado França, et al., Five Days of Ceftriaxone to Treat Spontaneous Bacterial Peritonitis in Cirrhotic Patients, Journal of Gastroenterology, Feb. 2002, p. 119-122 vol. 37, No. 2, Springer, Japan.

Clemmesen, et al., Cerebral Herniation in Patients With Acute Liver Failure is Correlated with Arterial Ammonia Concentration, Hepatology, Mar. 1999, p. 648-653, Vo. 29, No. 3, American Association for the Study of Liver Diseases.

EPO, Extended Search Report for Application No. 10014283.5, dated Mar. 10, 2011.

Garcia-Tsao, MD, et al., Management and Treatment of Patients with Cirrhosis and Portal Hypertension: Recommendations from the Department of Veterans Affairs Hepatitis C Resource Center Program and the National Hepatitis C Program, Am J Gastroenterol, 2009, p. 1802-1829, Vo. 104.

Intellectual Property Office of Singapore, Examination Report for Singapore Patent Application No. 200907712-4, dated Jan. 21, 2011.

Israel Patent Office, Office Action for Israeli Patent Application No. 183401, dated Jan. 6, 2011 (English Translation Only).

Jalan, et al., L-Ornithine Phenylacetate (OP): A Novel Treatment for Hyperammonemia and Hepatic Encephalopathy, Medical Hypotheses, 2007, p. 1064-1069, vol. 69, Elsevier Ltd.

Jalan, M.D., Rajiv, Intracranial Hypertension in Acute Liver Failure: Pathophysiological Basis of Rational Management, Seminars in Liver Disease, 2003, p. 271-282, vol. 23, No. 3, Thieme Medical Publishers, Inc., New York, NY, USA.

Jalan, R., et al., Treatment of Hyperammonemia in Liver Failure: A Tale of Two Enzymes, Gastroenterology, 2009, p. 2048-2051, vol. 1236.

Khan, et al., Frequency of Spontaneous Bacterial Peritonitis in Cirrhotic Patients with Ascites Due to Hepatitis C Virus and Efficacy of Cirpofloxacin in its Treatment, Gomal Journal of Medical Sciences, Jul.-Dec. 2009, p. 149-154, vol. 7, No. 2.

Lee et al., Acute Liver Failure: Summary of a Workshop, Hepatology, Apr. 2008, p. 1401-1415, vol. 47, No. 4.

Lee, W. M., Acetaminophen-Related Acute Liver Failure in the United States, Hepatology Research, 2008, p. S3-S8, vol. 38, Suppl. 1, The Japan Society of Hepatology.

Lukkarinen, M. et al., Oral Supplementation Corrects Plasma Lysine Concentrations in Lysinuric Protein Intolerance, Metabolism, Jul. 2003, p. 935-938, vol. 52, No. 7, Elsevier Inc.

Mexican Patent Office, Official Action for Mexican Patent Application No. MX/a/2007/006171, dated Oct. 2010.

Rogers, Q. R. et al., Deficiency of Pyrroline-5-Carboxylate Synthase in the Intestinal Mucosa of the Cat, The Journal of Nutrition, 1985, pp. 146-150, vol. 115, No. 1, American Institution of Nutrition.

Sanyal et al., Portosystemic Encephalopathy After Transjugular Intrahepatic Portosystemic Shunt: Results of a Prospective Controlled Study, Hepatology, 1994, p. 46-55, vol. 20, No. 1, Pt. 1, The American Association for the Study of Liver Diseases.

Sanyal, A. J., Prediction of Variceal Hemorrhage in Patients with Cirrhosis, UpToDate, Inc., Website (www.uptodate.com), Jan. 2010, UpToDate®.

Singh, et al., Changing Epidemiology and Predictors of Mortality in Patients With Spontaneous Bacterial Peritonitis at a Liver Transplant Unit, Clinical Microbiology and Infection, Jun. 2003, p. 531-537, vol. 9, No. 6., European Society of Clinical Microbiology and Infectious Diseases.

Stewart, P. M., et al., Effects of Arginine-Free Meals on Ureagenesis in Cats, American Journal of Physiological, 1981, p. E310-E315, vol. 241, No. 4, The American Physiological Society.

Stravitz, MD, et al., Intensive Care of Patients with Acute Liver Failure: Recommendations of the U.S. Acute Liver Failure Study Group, Critical Care Medicine, 2007, p. 2498-2508, vol. 35, No. 11, Lippincott Williams & Wilkins.

TDRdata.com, results from query of "Spontaneous Bacterial Peritonitis" in the epidemiological and references databases at www.tdrdata.com, retrieved on Jul. 27, 2010, p. 1-7.

Tuchman, M., et al., Management of Inherited Disorders of Ureagenesis, The Endocrinologist, 2002, p. 99-109, vol. 12, No. 2.

Albrecht et al., "Increase of the brain uptake index for L-ornithine in rates with hepatic encephalopathy," Neuroreport. (1994) 5(6): 671-673.

Albrecht et al., "Contrasting effects of thioacetamide-induced liver damage on the brain uptake indices of ornithine, arginine and lysine: modulation by treatment with ornithine aspartate," Metab Brain Dis. (1996) 11(3): 229-237.

Al-Hassnan et al., "The relationship of plasma glutamine to ammonium and of glycine to acid-base balance in propionic acidaemia," J. Inherit. Metab. Dis. (2003) 26: 89-91.

Anadiotis et al., "Ornithine transcarbamylase deficiency and pancreatitis," J Pediatr (2001) 138: 123-124.

Bachmann et al., "Ammonia toxicity to the brain and creatine," Molecular Genetics and Metabolism (2004) 81: S52-S57.

Batshaw et al., "Effect of sodium benzoate and sodium phenylacetate on brain serotonin turnover in the Ornithine transcarbamylase-deficient sparse-fur mouse," Pediatric Reserch (1988) 23(4): 368-374.

Batshaw et al., "Alternative pathway therapy for urea cycle disorders: twenty years later," J Pediatr (2001) 138(1): S46-S55.

Berry et al., "Long-term management of patients with urea cycle disorders," J Pediatri (2001) 138(1): S56-S61.

Brunquell et al., "Electroencephalographic findings in ornithine transcarbamylase deficiency," J Child Neurol (1999) 14(8): 533-536.

Brusilow et al., "Amino acid acylation: A mechanism of nitrogen excretion in inborn errors of urea synthesis," Science (1980) 207: 659-661.

Brusilow et al., "Treatment of episodic hyperammonemia in children with inborn errors of urea synthesis," The New England Journal of Medicine (1984) 310(25): 1630-1634.

Burlina et al., "Long-term treatment with sodium phenylbutyrate in ornithine transcarbamylase-deficient patients," Molecular Genetics and Metabolism (2001) 72: 351-355.

Cavarec et al., "Molecular cloning and characterization of a transcription factor for the *copia* retrotransposon with homology to the BTB-Containing Lola Neurogenic Factor," Mol. Cell. Biol. (1997) 17(1): 482-494.

Chen et al., "Continuous arteriovenous hemodiafiltration in the acute treatment of hyperammonaemia due to ornithine transcarbamylase deficiency," Renal Failure (2000) 22(6): 823-836.

DeJong et al., "Altered glutamine metabolism in rat portal drained viscera and hindquarter during hyperammonemia," Gastroenterology (1992) 103(3): 936-948.

Del Rosario et al., "Hyperammonemic encephalopathy after chemotherapy," J Clin Gastroenterol (1997) 25(4): 682-684.

Desjardins et al., "Effect of portacaval anastomosis on glutamine synthetase protein and gene expression in brain, liver and skeletal muscle," Metab Brain Dis. (1999) 14(4): 273-280.

Gebhardt et al., "Treatment of cirrhotic rats with L-Ornithine-L-Aspartate enhances urea synthesis and lowers serum ammonia levels," J Pharm Exp Thera. (1997) 283(1): 1-6.

Gordon, "Ornithine transcarbamylase deficiency: a urea cycle defect," European Journal of Paediatric Neurology (2003) 7: 115-121.

Grossi et al., "Amino acids mixtures in prevention of acute ammonia intoxication in dogs," Arch Surg (1967) 94: 261-266.

Hass et al., "Detection of subclinical and overt hepatic encephalopathy and treatment control after L-Ornithine-L-Aspartate medication by magnetic resonance spectroscopy (1H-MRS)," Z Gastroenterol (2005) 43: 373-378.

Häussinger et al., "Hepatic encephalopathy in chronic liver disease: a clinical manifestation of astrocyte swelling and low-grade cerebral edema?" J Hepatol. (2000) 32(6): 1035-1038.

Honda et al., "Successful teatment of severe hyperammonemia using sodium phenylacetate powder prepared in hospital pharmacy," Biol. Pharm. Bull. 25(9): 1244-1246, 2002.

Igarashi et al., "Determination of ornithine conjugates of some carboxylic acids in birds by high-performance liquid chromatography," Chem Pharm Bull (1992) 40(8): 2196-2198.

Iyer et al., "Mouse model for human arginase deficiency," Mol Cell Biol. (2002) 22(13): 4491-4498.

Jalan et al., "Acute-on-chronic liver failure: pathophysiological basis of therapeutic options," Blood Purif (2002) 20: 252-261.

Jalan et al., "The molecular pathogenesis of hepatic encephalopathy," The International Journal of Biochemistry & Cell Biology (2003) 35: 1175-1181.

James et al., "The conjugation of phenylacetic acid in man, sub-human primates and some non-primate species," Proc R Soc Lond B, (1972) 182: 25-35.

Kasumov et al., "New secondary metabolites of phenylbutyrate in humans and rats," Drug Metab Dispos. (2004) 32(1): 10-19.

MacArthur et al., "Pharmacokinetics of sodium phenylacetate and sodium benzoate following intravenous administration as both a bolus and continuous infusion to healthy adult volunteers," Molecular Genetics and Metabolism (2004) 81: S67-S73.

Maestri et al., "Prospective treatment of urea cycle disorders," J Pediatr. (1991) 119(6): 923-928.

Maestri et al., "Long-term treatment of girls with ornithine transcarbamylase deficiency," N Engl J Med. (1996) 335(12): 855-859.

Maier, "Therapie der hepatischen Enzephalopathie," Dtsch med Wschr. (1988) 113:1886-1889.

Mendenhall et al., "A new therapy for portal systemic encephalopathy," The American Journal of Gastroenterology (1986) 81(7): 540-543.

Mihm et al., "Effect of L-ornithine-L-aspartate (LOLA) on neurometabolites in hepatic encephalopathy (HE)," Hepatology (2001) 34(4): 543A.

Mizock et al., "Septic Encephalopathy—Evidence for altered phenylalanine metabolism and comparison with hepatic encephalopathy," Arch Intern Med (1990) 150: 443-449.

Mizutani et al., "Hyperargininemia: Clinical course and treatment with sodium benzoate and phenylacetic acid," Brain Dev. (1983) 5(6): 555-563.

Nance et al., "Ammonia production in germ-free Eck fistula dogs," Surgery (1971) 70(2): 169-174.

Olde Damink et al., "Interorgan ammonia and amino acid metabolism in metabolically stable patients with cirrhosis and a TIPSS," Hepatology (2002) 36(5): 1163-1171.

Olde Damink et al., "The kidney plays a major role in the hyperammonemia seen after simulated or actual GI bleeding in patients with cirrhosis," (2003) 37: 1277-1285.

Olde Damink et al., "Interorgan ammonia metabolism in liver failure," (2002) 41: 177-188.

Petrowski et al., "Pharmacologic amino acid acylation in the acute hyperammonemia of propionic acidemia," Journal of Neurogenetics (1987) 4: 87-96.

Plecko et al., "Partial N-acetylglutamate synthetase deficiency in a 13-year-old girl: diagnosis and response to treatment with N-carbamylglutamate," Eur J Pediatr. (1998) 157: 996-998.

Praphanphoj et al., "Three cases of intravenous sodium benzoate and sodium phenylacetate toxicity occurring in the treatment of acute hyperammonaemia," J Inherit Metab Dis. (2000) 23: 129-136.

Rees et al., "Effect of L-Ornithine-L-Aspartate on patients with and without TIPS undergoing glutamine challenge: a double blind, placebo controlled trial," Gut (2000) 47: 571-574.

Romero-Gómez et al., "Intestinal glutaminase activity is increased in liver cirrhosis and correlates with minimal hepatic encephalopathy," Journal of Hepatology (2004) 41: 49-54.

Rose et al., "L-Ornithine-L-Aspartate in experimental portal-systemic encephalopathy: therapeutic efficacy and mechanism of action," Metabolic Brain Disease (1998) 13(2): 147-157.

Rose et al., "L-Ornithine-L-Aspartate lowers plasma and cerebrospinal fluid ammonia and prevents brain edema in rats with acute liver failure," Hepatology (1999) 30(3): 636-640.

Rukmini Devi et al., "Region-specific changes in CNS muscarinic acetylcholine receptors in a rat model of hyperammonemia," Biochem Pharmacol. (1998) 56(2): 237-241.

Sarhan et al., "Effects of inhibition of ornithine aminotransferase on thioactamide-induced hepatogenic encephalopathy," Neurochem Res. (1993) 18(4): 539-549.

Scaglia et al., "Effect of alternative pathway therapy on branched chain amino acid metabolism in urea cycle disorder patients," Mol Genet Metabolism (2004) 81: S79-S85.

Sears et al., "Disruption of the blood-brain barrier in hyperammonaemic coma and the pharmacologic effects of dexamethasone and difluoromethyl ornithine," J Neurosci Res. (1985) 14(2): 255-261.

Seiler et al., "Ornithine aminotransferase activity, liver ornithine concentration and acute ammonia intoxication," Life Sciences (1989) 45(11): 1009-1020.

Sen et al., "The pathophysiological basis of acute-on-chronic liver failure," Liver (2002) 22(Suppl. 2): 5-13.

Shawcross et al., "Hyperammonemia impairs neutrophil function," Hepatology (2005) 42: 537A.

Simell et al., "Waste nitrogen excretion via amino acid acylation: benzoate and phenylacetate in lysinuric protein intolerance," Pediatric Research (1986) 20(11): 1117-1121.

Smith et al., "The treatment of inborn errors of the urea cycle," Nature (1981) 291(5814): 378-380.

Soláini et al., "Variations in the plasma concentration of ornithine, citrulline and arginine in acute experimental liver failure," [Article in Italian] Boll Soc Ital Biol Sper. (1981) 57(7): 705-710.

Sugarbaker et al., "The role of the small intestine in ammonia production after gastric blood administration," Ann Surg. (1987) 206(1): 5-17.

Svanberg et al., "Effects of amino acids on synthesis and degradation of skeletal muscle proteins in humans," Am J Physiol. (1996) 271(4 Pt1): E718-724.

Tuchman, MD et al., "Episodic hyperammonemia in adult siblings with hyperornithinemia, hyperammonemia, and homocitrullinuria syndrome," Arch Neurol. (1990) 47: 1134-1137.

Vogels et al., "L-ornithine vs L-ornithine-L-aspartate as a treatment for hyperammonemia-induced encephalopathy in rats," J Hepatology, (1997) 26(1): 174-182.

Zieve et al., "Conditional deficiencies of ornithine or ornithine or arginine," J Am Coll Nutr. (1986) 5(2): 167-176.

International Search Report and Written Opinion received in PCT/US2010/029708 dated Jun. 3, 2010.

Damink et al., Stimulated Liver and Muscle Protein Synthesis by Intravenous Isoleucine Supplementation During a Simulated Variceal Bleed in Patients with Cirrhosis of the Liver, Hepatology, Oct. 2001, AASLD Abstracts #50.

Mizock, MD, FACP, Nutritional Support in Hepatic Encephalopathy, Nutrition, 1999, pp. 220-228, vol. 15, No. 3, Elsevier Science Inc.

Intellectual Property Office of Singapore (IPOS) Search Report and Written Opinion, dated Apr. 23, 2010, Singapore Patent Application No. 200907712-4.

EPO, Office Communication, dated Feb. 13, 2012, for EPO Application No. 10 014 283.5-2123.

EPO Examination Report, dated Jan. 27, 2012 from EP Patent Application No. 09 013 613.6-2123.

* cited by examiner

Arterial ammonia in BDL rats

Plasma Ornithine (µM)

COMPOSITIONS COMPRISING ORNITHINE AND PHENYLACETATE OR PHENYLBUTYRATE FOR TREATING HEPATIC ENCEPHALOPATHY

This Application is the National Phase Application of International Application No. PCT/GB2005/004539 filed Nov. 28, 2005, which claims priority to Patent Application in United Kingdom No. 0426141.8 filed Nov. 26, 2004 and to Patent Application in United Kingdom No. 0426142.6 filed Nov. 26, 2004.

FIELD OF THE INVENTION

The present invention relates to the prevention or treatment of liver decompensation or hepatic encephalopathy.

BACKGROUND OF THE INVENTION

Chronic liver disease is characterised by the gradual destruction of liver tissue over time, whereby healthy and regenerating liver tissue is slowly replaced with scar and necrotic tissue. This is known as liver cirrhosis. Normal liver function is impaired and the scar tissue progressively diminishes blood flow through the liver. As normal regenerating liver tissue is lost, nutrients, hormones, drugs and toxins are no longer effectively processed.

This can result in symptoms including abnormal clearance of proteins absorbed through the intestinal tract, leading to accumulation of ammonia; abnormal excretion, leading to an accumulation of bilirubin in the blood, producing jaundice; increased sinusoidal pressure, leading to fluid accumulation in the abdomen (ascites); and portal hypertension (and portosystemic shunting) wherein scarred liver tissue acts as a barrier to blood flow, leading to increased portal blood pressure and oesophageal varices.

Patients with chronic liver disease can be in a fairly stable clinical state and exhibit few or no symptoms. However, such patients are at risk of an abrupt deterioration in their condition which can lead to acute-on-chronic liver failure. This transition from a "compensated" state, where the liver is able to function, albeit at a reduced level, to a "decompensated" state, where liver function fails, involves the effect of precipitating events. Precipitating events associated with chronic liver disease include gastrointestinal bleeding, infection (sepsis), portal vein thrombosis and dehydration.

For example, 50% of patients with cirrhosis of the liver have oesophageal varices and in a third of these patients, the oesophageal varices will burst and cause gastrointestinal bleeding within two years of diagnosis (Grace N D (1992) Gastroenterol Clin North Am 21: 149-161). An upper gastrointestinal bleed is known to increase the susceptibility to life-threatening complications such as bacterial peritonitis, sepsis, renal failure and hepatic encephalopathy (Teran et al. (1997) Gastroenterology 112: 473-482; Garden et al. (1985) Br J Surg 72: 91-95; Pauwels et al. (1996) Hepatology 24: 802-806; Bleichner et al. (1986) Br J Surg 73: 724-726) resulting in the death of about 30% of patients despite adequate control of bleeding (Grace 1992 supra).

Hepatic encephalopathy (HE) is a complex neuropsychiatric disorder that occurs in diverse clinical situations such as acute or chronic liver disease and spontaneous portosystemic venous shunting. In the early stages of hepatic encephalopathy subtle mental changes occur such as poor concentration, confusion and disorientation. In severe cases, hepatic encephalopathy can lead to stupor, coma, brain swelling (cerebral edema) and death. In the case of patients who develop HE as a result of chronic liver disease, the onset of HE is often the result of a clinically precipitating event such as gastrointestinal bleeding, sepsis (infection), portal vein thrombosis or dehydration.

Gastrointestinal bleeding and portosystemic shunting allows toxic substances, which are usually metabolised by the liver, to bypass the liver, enter the systemic circulation and cross the blood-brain barrier to exert direct or indirect neurotoxic effects on the central nervous system. Ammonia accumulation is thought to play an important role in the progression of hepatic encephalopathy and multiorgan failure (respiratory failure, cardiovascular failure, kidney failure). In addition to ammonia, septicaemia (or bacterial peritonitis) which develops soon after a gastrointestinal bleed is also likely to be a contributing factor to hepatic encephalopathy.

Liver decompensation can then lead to multiorgan failure and hepatic encephalopathy. In the early stages of hepatic encephalopathy subtle mental changes such as poor concentration or the inability to construct simple objects occurs. In severe cases, hepatic encephalopathy can lead to stupor, coma, brain swelling and death.

The prognosis for patients with chronic liver disease is difficult to estimate because the condition has many causes. Preventative measures to minimise progression from the compensated state to the decompensated state include avoidance of further causative agents which will worsen the condition, such as complete abstinence from alcohol and vaccination against hepatitis A and B.

However, once liver decompensation occurs, the chances of survival are reduced and liver transplantation is the only treatment that can extend life. Since it is liver decompensation that leads to a reduced life expectancy, it is highly desirable to prevent liver decompensation from occurring.

A common therapy for patients with hepatic encephalopathy involves strategies to reduce the concentration of ammonia. These include restriction of dietary protein intake; administration of lactulose, neomycin, L-ornithine L-aspartate (LOLA), or sodium benzoate; and cleansing enemas.

SUMMARY OF THE INVENTION

The present invention concerns the use of ornithine and at least one of phenylacetate and phenylbutyrate to prevent or treat liver decompensation or hepatic encephalopathy (HE) in patients. Isoleucine may also be administered to those patients further having an isoleucine deficiency attributable, for example to gastrointestinal bleeding. Accordingly, the invention provides:

use of ornithine in the manufacture of a medicament for use in combination with at least one of phenylacetate and phenylbutyrate for preventing or treating liver decompensation or hepatic encephalopathy;

use of at least one of phenylacetate and phenylbutyrate in the manufacture of a medicament for use in combination with ornithine for preventing or treating liver decompensation or hepatic encephalopathy;

use of ornithine and at least one of phenylacetate and phenylbutyrate in the manufacture of a medicament for preventing or treating liver decompensation or hepatic encephalopathy;

products containing ornithine and at least one of phenylacetate and phenylbutyrate for simultaneous, separate or sequential use for preventing or treating liver decompensation or hepatic encephalopathy;

a pharmaceutical composition comprising ornithine and at least one of phenylacetate and phenylbutyrate;

an agent for preventing or treating liver decompensation or hepatic encephalopathy, comprising ornithine and at least one of phenylacetate and phenylbutyrate; and a method of treating a patient having or at risk of having liver decompensation or hepatic encephalopathy, which method comprises administering an effective amount of ornithine and at least one of phenylacetate and phenylbutyrate to said patient.

DETAILED DESCRIPTION OF THE INVENTION

Figure 1:
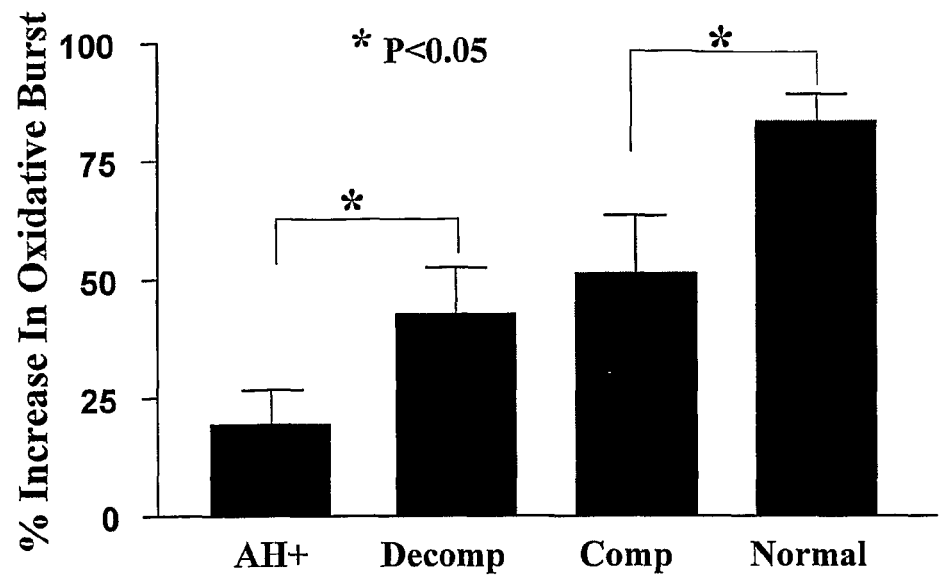
FIG. 1 shows that neutrophil function is altered in patients with cirrhosis and worsens with increasing severity of liver disease.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The present invention is concerned with the early treatment of patients with liver disease, before development of liver decompensation and thus before hepatic encephalopathy has occurred, to prevent or delay the onset of liver decompensation. Alternatively, the present invention is concerned with treatment of hepatic encephalopathy by effectively reducing ammonia concentration and maintaining neutrophil function.

Subjects to be Treated

The present invention is concerned with the prevention or treatment of liver decompensation or hepatic encephalopathy. The subject's liver may therefore be in the compensated state. The subject may have chronic liver disease. The subject may have liver cirrhosis. The subject may have acute liver failure. The subject to be treated may have hepatic encephalopathy.

The onset of both acute and chronic liver disease may be due to a xenobiotic cause. For example, the subject may have been exposed to a chemical, drug or some other agent which causes liver damage. The subject may have a reaction to an over-the-counter, prescriptive or "recreational" drug which causes liver damage. The subject may have been taking Rezulin™ (troglitazone; Parke-Davis), Serzone™ (nefazodone; Bristol-Myers Squibb) or other drugs thought to cause liver damage. The subject may be one who has had an overdose of a particular drug or exceeded the recommended dosage of a drug capable of causing liver damage. For example, the subject may have taken an overdose of paracetamol. The subject may have been exposed to chemicals which can cause liver damage such as, for example, at their place of work. For example, the subject may have been exposed to such chemicals in an industrial or agricultural context. The subject may have consumed plants which contain compounds which can cause liver damage, in particular this may be the case where the subject is an animal, such as a herbivore. For example, the subject may have consumed a plant containing pyrrolizidine alkaloid such as ragwort. The subject may have been exposed to environmental toxins thought to cause liver disease.

Drug-related liver toxicity comprises more than 50% of all cases with acute liver disease (acute liver failure). Acetaminophen-(also known as paracetamol and N-acetyl-p-aminophenol) toxicity is the most common cause of acute liver failure in the United States and Great Britain. Long-term moderate to heavy alcohol users who take acetaminophen in therapeutic or modestly excessive doses are at risk of severe hepatic injury and possibly acute liver failure. Alcohol use potentiates the toxic effects of acetaminophen. Idiosyncratic drug toxicity also contributes to acute liver failure. Idiosyncratic drug toxicity is thought to be a hypersensitivity response wherein the subject responds to a drug in a pharmacologically abnormal way. This abnormal response can lead to acute liver failure.

The acute liver failure or chronic liver disease may be caused by infection with a pathogenic organism. For example, the liver disease may be due to viral infection. In particular, the subject may be infected, or have been infected, with a virus which causes hepatitis. The subject may have chronic viral hepatitis. The virus may, for example, be hepatitis B, C or D virus. In some cases, and in particular where the subject has viral hepatitis, the subject may also be infected with HIV-I or II. The subject may have AIDS. It is possible that the subject may have been, or be, infected with other organisms which cause liver disease and in particular those which are present in the liver during some stage of their life cycle. For example, the subject may have, or have had, liver fluke.

The subject may have an inherited disease which causes, or increases the risk of, chronic liver disease. For example, the subject may have one or more of hepatic hemochromatosis, Wilson's disease or $\alpha$-1-antitrypsin deficiency. The subject may have an inherited disorder which causes some kind of structural or functional abnormality in the liver which increases the likelihood of liver fibrosis. The subject may be genetically predisposed to develop an autoimmune disorder which damages the liver and hence which can contribute to liver fibrosis.

The chronic liver disease may be alcohol-induced. A man or woman to be treated may be, or have been, an alcoholic. He or she may be, or have been, consuming on average 50 or more units of alcohol per week, 60 or more units of alcohol per week, 75 or more units of alcohol per week and even 100 or more units of alcohol per week. The man or woman may be, or have been, consuming on average up to 100 units of alcohol per week, up to 150 units of alcohol per week and even up to 200 units of alcohol per week. The measurement of one unit of alcohol differs from country to country. Here, one unit equals 8 grams of ethanol in accordance with the United Kingdom standard.

The man or woman may have been consuming such levels of alcohol for 5 or more years, 10 or more years, 15 or more years or 20 or more years. The subject may have been consuming such levels of alcohol for up to 10 years, up to 20 years, up to 30 years and even up to 40 years. In cases of alcohol-induced liver cirrhosis the subject may be aged, for example, 25 years or over, 35 years or over, 45 years or over and even over 60 years.

The subject may be male or female. Women may be more susceptible to the adverse effects of alcohol than men. Women can develop alcoholic chronic liver disease in a shorter time frame and from smaller amounts of alcohol than men. There seems to be no single factor to account for increased susceptibility to alcoholic liver damage in females, but the effect of hormones on the metabolism of alcohol may play an important role.

In other embodiments of the invention, the subject may have one or more of a number of other conditions known to result in liver damage such as, for example, primary biliary cirrhosis, autoimmune chronic active hepatitis, and/or schistosomiasis (parasitic infection). The subject may have or have had a bile duct blockage. In some cases, the underlying cause of chronic liver disease may not be known. For example the subject may have been diagnosed as having cryptogenic cirrhosis. In one embodiment, the subject may be suspected of having any of the conditions listed herein.

Methods for diagnosing chronic liver disease, acute liver failure and hepatic encephalopathy are well known in the art and in particular to clinicians and veterinarians in the field. Preferably, the subject will have been diagnosed as having a liver disease and hepatic encephalopathy, for example by a medical or veterinarian professional. The subject may display one or more symptoms associated with liver disease such as one or more of jaundice, ascites, skin changes, fluid retention, nail changes, easy bruising, nose bleeds, oesophageal varices, and in male subjects may have enlargement of breasts. The subject may display exhaustion, fatigue, loss of appetite, nausea, weakness and/or weight loss. The subject may also display one or more symptoms associated with hepatic encephalopathy such as one or more of confusion, disorientation, dementia, stupor, coma, cerebral edema, multiorgan failure (respiratory failure, cardiovascular failure or kidney failure), muscle stiffness/rigidity, seizures or speech impairment. The subject to be treated may or may not be taking other drugs to treat liver disease. The subject to be treated may be at risk of developing hepatic encephalopathy.

The liver disease may have been, or be, confirmed by physical examination including techniques such as ultrasound. Liver biopsies may have been taken to look for build up of fibrosis, necrotic cells, cellular degeneration and/or inflammation and other characteristic features of liver disease. Liver function may have been assessed in the subject to determine whether this is compromised in the subject. The nature and underlying cause of the liver disease may be characterized. Any history of exposure to causative agents of liver disease may be determined.

The subject to be treated may be at risk for hepatic encephalopathic episodes, for example patients who are awaiting liver transplants, surgical and/or portal hypertension patients. A person at risk for hepatic encephalopathic episodes is a person who has not suffered any hepatic encephalopathic episodes or has not suffered any hepatic encephalopathic episode for an extended period of time (about 12 weeks or longer), but has a disorder or medical condition which creates a risk of hepatic encephalopathic episodes. A hepatic encephalopathic episode is a clinical condition characterised by the presence of cerebral dysfunction in patients with liver disease or dysfunction. There is a wide spectrum of mental disturbances in hepatic encephalopathy which range from minimal where the main effects are a reduction in the quality of life, to overt which leads to coma and ultimately death.

Scoring systems may be used to assess the severity of liver disease and hepatic encephalopathy and also the prognosis of subjects. The Child-Pugh, West Haven Criteria, Glasgow Coma Scale or modified Child-Pugh scoring system may be used. Alternatively, the (APACHE) II scoring system may be used. Points are assigned to parameters including serum bilirubin levels, serum albumin levels and to signs including presence of ascites or encephalopathy. Subjects to be treated may be classified in Child-Pugh class A, B or C. Generally subjects to be treated are classified in Child-Pugh class C.

A man or woman to be treated may be aged, for example from 25 to 80 years. In one embodiment, the man or woman is aged from 45 to 70 years. In another embodiment, the man or woman is aged from 25 to 44 years. In a further embodiment, the man or woman is aged over 65 years.

The invention does have veterinary use, however. The subject to be treated may be a farm animal for example, a cow or bull, sheep, pig, ox, goat or horse or may be a domestic animal such as a dog or cat. The subject may or may not be an animal model for liver disease. The animal may be any age, but will often be a mature adult subject.

Formulation

The amino acids used in the present invention may be pure crystalline amino acids. In general, the amino acids are in the L-form, rather than the D-form, or a mixture of D and L. Isolated forms of the amino acids are typically used. Any active form of the amino acid may be used to prevent or treat the liver decompensation or hepatic encephalopathy. A pharmaceutically acceptable form of the amino acid may be used. The amino acids may be employed as free amino acids or amino acid salts or derivatives.

Ornithine may be in pure crystalline amino acid form. In general, ornithine is in the L-form, rather than the D-form, or a mixture of D and L. Isolated forms of ornithine are typically used. Any active form of ornithine may be used or a pharmaceutically acceptable form of ornithine may be used. Ornithine may be employed as a free amino acid or an amino acid salt or derivative.

Typically, ornithine is used as a single, monomeric amino acid. Ornithine may be used in salt form, for example ornithine hydrochloride may be used. Ornithine may be in the form of a physiologically acceptable salt in free form. Therefore, the ornithine or the ornithine salt are typically not chemically bound, or covalently linked to any other agent.

Derivatives of ornithine may be used. For example, keto or hydroxy analogs of ornithine may be administered as sodium or calcium salts. Keto acids of ornithine include ornithine ketoglutarate, ornithine ketoleucine and ornithine ketovaline. Salts or derivatives of ornithine may be used in place of or in addition to free ornithine.

At least one of phenylacetate and phenylbutyrate may be used. Phenylacetate and/or phenylbutyrate may be in physiologically acceptable salt form, such as an alkali metal or alkaline earth metal salt. The salt may be sodium phenylacetate or sodium phenylbutyrate. The salt form of phenylacetate and phenylbutyrate may be in free form. Therefore the phenylacetate and phenylbutyrate or phenylacetate salt and phenylbutyrate salt are typically not chemically bound, or covalently linked to any other agent.

Optionally isoleucine is used. Isoleucine may be in pure crystalline amino acid form. In general, isoleucine is in the L-form, rather than the D-form, or a mixture of D and L. Isolated forms of isoleucine are typically used. Any active form of isoleucine may be used or a pharmaceutically acceptable form of isoleucine may be used. Isoleucine may be employed as a free amino acid or an amino acid salt or derivative.

Typically, isoleucine is used as a single, monomeric amino acid. Isoleucine may be used in salt form, for example isoleucine hydrochloride may be used. Isoleucine may be in the form of a physiologically acceptable salt in free form. Therefore, the isoleucine or the isoleucine salt are typically not chemically bound, or covalently linked to any other agent.

Pharmaceutical Compositions

The ornithine and the phenylacetate and/or phenylbutyrate are typically formulated for administration with a pharmaceutically acceptable carrier or diluent. The ornithine and the phenylacetate and/or phenylbutyrate may thus be formulated as a medicament with a standard pharmaceutically acceptable carrier(s) and/or excipient(s) as is routine in the pharmaceutical art. The exact nature of the formulation will depend upon several factors including the desired route of administration. Typically, ornithine and the phenylacetate and/or phenylbutyrate are formulated for oral, intravenous, intragastric, intravascular or intraperitoneal administration.

The pharmaceutical carrier or diluent may be, for example, an isotonic solution such as physiological saline. Solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with ornithine and at least one of phenylacetate and phenylbutyrate, a pharmaceutically acceptable carrier, e.g. sterile water, olive oil, ethyl oleate, glycols, e.g. propylene glycol, and if desired, a suitable amount of lidocaine hydrochloride.

Medicaments of the invention can comprise ornithine as the only amino acid component. Medicaments of the invention can comprise ornithine and isoleucine as the only amino acid components. The medicament may consist essentially of ornithine and at least one of phenylacetate and phenylbutyrate. The medicament may consist essentially of ornithine, isoleucine and at least one of phenylacetate and phenylbutyrate.

The medicament may consist essentially of ornithine, phenylacetate and/or phenylbutyrate and a pharmaceutically acceptable carrier. Such a medicament therefore contains substantially no other amino acid in addition to ornithine. The medicament may consist essentially of ornithine, isoleucine, phenylacetate and/or phenylbutyrate and a pharmaceutically acceptable carrier. Such a medicament therefore contains substantially no other amino acid in addition to ornithine and isoleucine.

The phenylacetate may be present in an amount from 5 to 100%, for example from 10 to 50%, or 20 to 40%, by weight of the weight of ornithine. The phenylbutyrate may be present in an amount from 5 to 100%, for example from 10 to 50%, or 20 to 40%, by weight of the weight of ornithine.

However, the medicament may comprise free aspartate, glutamate or arginine in non-peptide form, typically in an insubstantial amount. Generally, the amount by weight of aspartate, glutamate or arginine does not exceed the amount by weight of ornithine. By an insubstantial amount, it is meant that the amount by weight of aspartate, glutamate or arginine, or a combination of these amino acids, does not exceed 20% by weight of ornithine. Therefore, the medicament may comprise substantially no aspartate. In one embodiment, the composition does not comprise aspartate, glutamate or arginine. Trace amounts of aspartate, glutamate or arginine may be present in the composition. By trace amount, it is meant that the amount by weight of aspartate, glutamate or arginine, or a combination of these amino acids, does not exceed 1% by weight of ornithine. Preferably, the amount by weight of aspartate, glutamate or arginine does not exceed 0.5% by weight of ornithine.

In another embodiment, the composition may comprise yet other amino acids in non-peptide form, typically as the free amino acid or a physiologically acceptable salt thereof in free form. The amount of these other amino acids generally does not exceed the amount by weight of ornithine. For example, the other amino acids may be present in an amount by weight up to 20%, for example from 5 to 20%, of the weight of ornithine. Such other amino acids that may be present in the composition include essential and non-essential amino acids. The composition may comprise other branched chain amino acids (BCAAs). BCAAs include isoleucine, valine and leucine. Thus, a composition of the invention may further comprise isoleucine and/or valine and/or leucine.

Treatment

Ornithine and at least one of phenylacetate and phenylbutyrate are administered in combination to a subject for preventing or delaying the onset of liver decompensation or hepatic encephalopathy. Ornithine and at least one of phenylacetate and phenylbutyrate can thus be administered in combination to improve the condition of a subject, for example a subject suffering from chronic liver disease following a precipitating event. Ornithine and at least one of phenylacetate and phenylbutyrate may be administered in combination to alleviate the symptoms of a subject, for example the symptoms associated with chronic liver disease in a subject following a precipitating event. Ornithine and at least one of phenylacetate and phenylbutyrate may be administered in combination to combat or delay the onset of liver decompensation or hepatic encephalopathy.

Ornithine and at least one of phenylacetate and phenylbutyrate may be administered in combination to a subject for treatment of hepatic encephalopathy. Ornithine and at least one of phenylacetate and phenylbutyrate may be administered in combination to improve the condition of a patient suffering from hepatic encephalopathy. Ornithine and at least one of phenylacetate and phenylbutyrate may be administered in combination to alleviate the symptoms associated with hepatic encephalopathy. Ornithine and at least one of phenylacetate and phenylbutyrate may be administered in combination to combat hepatic encephalopathy. Ornithine and at least one of phenylacetate and phenylbutyrate may be administered in combination to prevent an initial hepatic encephalopathic episode in a person at risk of for hepatic encephalopathic episodes. Ornithine and at least one of phenylacetate and phenylbutyrate may be administered in combination lessen the severity of an initial hepatic encephalopathic episode in a person at risk of for hepatic encephalopathic episodes. Ornithine and at least one of phenylacetate and phenylbutyrate may be administered in combination to delay an initial hepatic encephalopathic episode in a person at risk of for hepatic encephalopathic episodes.

Development of liver decompensation and hepatic encephalopathy involves "precipitating events" (or "acute attacks"). Such precipitating events include gastrointestinal bleeding, infection (sepsis), portal vein thrombosis and dehydration. The onset of such an acute attack is likely to lead to hospitalisation. The patient may suffer one of these acute attacks or a combination of these acute attacks.

A subject who has had or is suspected of having had an acute attack is treated according to the invention with ornithine and phenylacetate and/or phenylbutyrate in combination to prevent progression of the liver to the decompensated state. The invention can therefore prevent the medical consequences of liver decompensation such as hepatic encephalopathy. The ornithine and phenylacetate and/or phenylbutyrate may be used to preserve liver function. Use of ornithine and phenylacetate and/or phenylbutyrate may thus extend the life of a patient with liver disease. In one embodiment, the metabolic consequences of a gastrointestinal bleed such as hyperammonemia, hypoisoleucemia and reduced protein synthesis in the post-bleeding period are prevented.

Typically, treatment of subjects may begin as soon as possible after the onset or the suspected onset of a precipitating event (acute attack). Preferably, treatment of the subject begins prior to repeated acute attacks. More preferably, treatment of the subject begins following the first acute attack.

Treatment is typically given promptly after the start of an acute attack. Treatment may begin after the symptom(s) of an acute attack or suspected acute attack have been detected e.g. by a medic such as a physician, a paramedic or a nurse. Treatment may begin upon hospitalisation of the subject. Treatment may thus begin within 6 hours, within 3 hours, within 2 hours or within 1 hour after the symptom(s) of an acute attack or suspected acute attack have been detected. Treatment of the subject may therefore begin from 1 to 48 hours, for example from 1 to 36 hours or from 1 to 24 hours after the symptom(s) of an acute attack or suspected acute attack have been detected.

Treatment may occur for up to 8 weeks, for example up to 6 weeks, up to 4 weeks or up to 2 weeks after the symptom(s) of an acute attack or suspected acute attack have been detected. Treatment may therefore occur for up to 48 hours, for example for up to 36 hours or for up to 24 hours after the symptom(s) of an acute attack or suspected acute attack have been detected. Typically, treatment occurs to the time when recovery from the acute precipitating event is evident.

The subject is treated with the ornithine and the phenylacetate and/or phenylbutyrate. Ornithine and at least one of phenylacetate and phenylbutyrate may be administered in combination in a single medicament, or separately in two or three different medicaments. Where ornithine and at least one of phenylacetate and phenylbutyrate are to be administered in a combined medicament, the combination may be prepared immediately before administration, or may be stored as a combined medicament.

Where the ornithine and the phenylacetate and/or phenylbutyrate are to be administered separately, the medicaments may be administered simultaneously or sequentially over a period of time. Two or three separate medicaments may be administered over a period of time.

Where two medicaments are administered, ornithine may be administered first, followed by administration of the phenylacetate and phenylbutyrate, the phenylacetate or the phenylbutyrate. Alternatively, the phenylacetate and phenylbutyrate, the phenylacetate or the phenylbutyrate may be administered first, followed by ornithine. In another embodiment, a combination of ornithine and phenylacetate may be administered first, followed by administration of phenylbutyrate. Alternatively, a combination of ornithine and phenylbutyrate may be administered first, followed by administration of phenylacetate. In another embodiment, phenylacetate may be administered first, followed by administration of a combination of ornithine and phenylbutyrate. Alternatively, phenylbutyrate may be administered first, followed by administration of a combination of ornithine and phenylacetate.

Where three medicaments are administered, ornithine, phenylacetate and phenylbutyrate are administered at separate times. Ornithine may be administered first, second or third. Where ornithine is administered first, phenylacetate or phenylbutyrate may be administered second, followed by administration of phenylbutyrate or phenylacetate. Where ornithine is administered second, phenylacetate or phenylbutyrate are administered first, and phenylbutyrate or phenylacetate are administered third. Where ornithine is administered third, phenylacetate or phenylbutyrate are administered first, and phenylbutyrate or phenylacetate are administered second.

The second medicament may be administered up to 5 hours, such as up to 2 hours or up to 1 hour, following administration of the first medicament. The second medicament can thus be administered from 15 minutes to 5 hours, for example from 30 minutes to 4 hours or from 1 hour to 3 hours, following administration of the first medicament.

The third medicament may be administered up to 5 hours, such as up to 2 hours or up to 1 hour, following administration of the second medicament. The third medicament can thus be administered from 15 minutes to 5 hours, for example from 30 minutes to 4 hours or from 1 hour to 3 hours, following administration of the second medicament.

The medicaments of the invention may be administered at the same site or at different sites. The medicaments of the invention may be administered via the same route or by different routes. A medicament of the invention may be administered by any suitable route. Preferably it is administered by oral, intravenous, intragastric, intraperitoneal or intravascular routes. For example, when ornithine and at least one of phenylacetate and phenylbutyrate are administered separately, they may all be administered orally or they may all be administered intravenously or ornithine may be administered orally and the phenylacetate and/or phenylbutyrate may be administered intravenously, or the phenylacetate and/or phenylbutyrate may be administered orally and ornithine may be administered intravenously.

Therapeutically effective amounts of ornithine, the phenylacetate and/or phenylbutyrate and the optional isoleucine are administered to the subject. The doses of the ornithine, the phenylacetate and/or phenylbutyrate and the isoleucine can be determined according to various parameters such as the age, weight and condition of the subject to be treated; the type and severity of the liver disease; the route of administration; and the required regimen.

A typical dose of ornithine, of phenylacetate or phenylbutyrate, or of isoleucine is from 0.02 to 1.25, for example from 0.1 to 0.5, g per kg of body weight, depending on such parameters. Consequently, a dosage of ornithine, of phenylacetate or phenylbutyrate, or of isoleucine may be from 1 g to 50 g such as from 5 g to 30 g. The dosage of ornithine may be 10 to 30 g. The dose of isoleucine may be 5 to 15 g. The ornithine and phenylacetate/phenylbutyrate may be administered in a weight ratio from 10:1 to 1:10 such as from 5:1 to 1:5 or from 2:1 to 1:2 or about 1:1. A physician will be able to determine the required dosage of ornithine and of phenylacetate or phenylbutyrate and of the optional isoleucine for any particular subject.

A single dose of ornithine and a single dose of phenylacetate and/or phenylbutyrate may be administered. Optionally, a single dose of isoleucine may also be administered. Alternatively multiple doses, for example two, three, four or five doses, of ornithine and/or of the phenylacetate and/or phenylbutyrate and/or of the optional isoleucine may be administered. Such multiple doses may be administered over a period of one month or two weeks or one week. In another embodiment, a single dose or multiple doses such as two, three, four or five doses of ornithine and/or of phenylacetate and/or phenylbutyrate may be administered daily.

Other amino acids may be administered to a subject as noted above. The or each such other amino acid may be administered in the same medicament as the ornithine and/or the phenylacetate and/or phenylbutyrate, or may be administered separately. When administered separately, the or each other amino acid may be given simultaneously with, or at a different time such as up to 5 hours, up to 2 hours or up to 1 hour before or after, the administration of ornithine and/or phenylacetate and/or phenylbutyrate. The or each other amino acid is typically administered orally or intravenously.

A therapeutically effective amount of the or each other amino acid is administered to the subject. The dose will be dependent upon various parameters such as those noted above for ornithine, phenylacetate and phenylbutyrate. A typical dose of the or each other amino acid is from 0.02 to 1.25, for example from 0.1 to 0.5, g per kg of bodyweight. A dosage of the or each other amino acid may therefore be from 1 g to 50 g such as 5 g to 30 g.

A single dose of the or each other amino acid may be administered. Alternatively, multiple doses, for example two, three, four or five doses may be administered. Such multiple doses may be administered over a period of one month or two weeks or one week. In another embodiment, a single dose or multiple doses such as two, three, four or five doses may be administered daily.

The following Examples illustrate the invention.

EXAMPLE 1

Neutrophil Function is Altered in Patients with Cirrhosis and Worsens with Increasing Severity of Liver Disease Methods for Measurement of Neutrophil Phagocytosis and Oxidative Burst Phagotest: Heparinised whole blood was incubated with opsonised FITC-labelled *E coli* and CD16. The cells were then analysed by flow cytometry (FACScan Becton Dickinson), gated through forward and side scatter and subsequently assessed on the basis of R-phycoerythrin (PE) [Immunotech, Marseille, France] flurochrome expression to identify CD16 positive cells. The gated population was then assessed for the presence of FITC-labelled bacteria.

Phagoburst: Heparinised whole blood was incubated with opsonised *E coli* suspension to stimulate oxidative burst. A substrate solution was added to determine the conversion of dihydrorhodamine (DHR) 123 to the flurogenic compound Rhodamine (R) 123. The reaction was stopped and fixed before incubation with CD16 antibody for positive neutrophil identification. Analysis was then undertaken by flow cytometry.

Neutrophil Chemotaxis: Neutrophil chemotaxis was measured using a modified Boyden chamber method using interleukin-8 as chemo-attractant to stimulate chemokinesis.

Patients and Methods

We studied 30 patients with cirrhosis (Alcoholic cirrhosis; mean age 53.2 (SEM 4.6) and 20 healthy volunteers. Patients with cirrhosis were classified as those with superimposed alcoholic hepatitis (AH+) and those with decompensated or compensated livers. Phagotest was used to determine the phagocytic capacity and Phagoburst was used to determine whether the cells were able to generate oxidative burst when exposed to *E coli*.

Results

We observed that neutrophils from cirrhotic patients had a significantly reduced ability to phagocytose bacteria. We also found that patients with cirrhosis had a reduced capacity to respond to stimulation of the neutrophils by *E coli* in terms of increasing the rate of generation of oxidative burst (FIG. 1). This reduction in capacity correlated with the severity of liver disease indicating that the more advanced the stage of liver disease, the less the ability to respond to and cope with infection.

EXAMPLE 2

Ammonia Reduces Phagocytic Capacity in Neutrophils

Methods for Measurement of Neutrophil Phagocytosis and Oxidative Burst

As in Example 1.

Patients and Methods

Blood was collected from healthy volunteers (n=15) and incubated for 1 hour with increasing concentrations of ammonia. The ability of the neutrophils to phagocytose bacteria was measured using the Phagotest and Neutrophil chemotaxis assays. 10 ng/ml IL-8 was used in the Neutrophil chemotaxis assay.

Results

Figure 2:
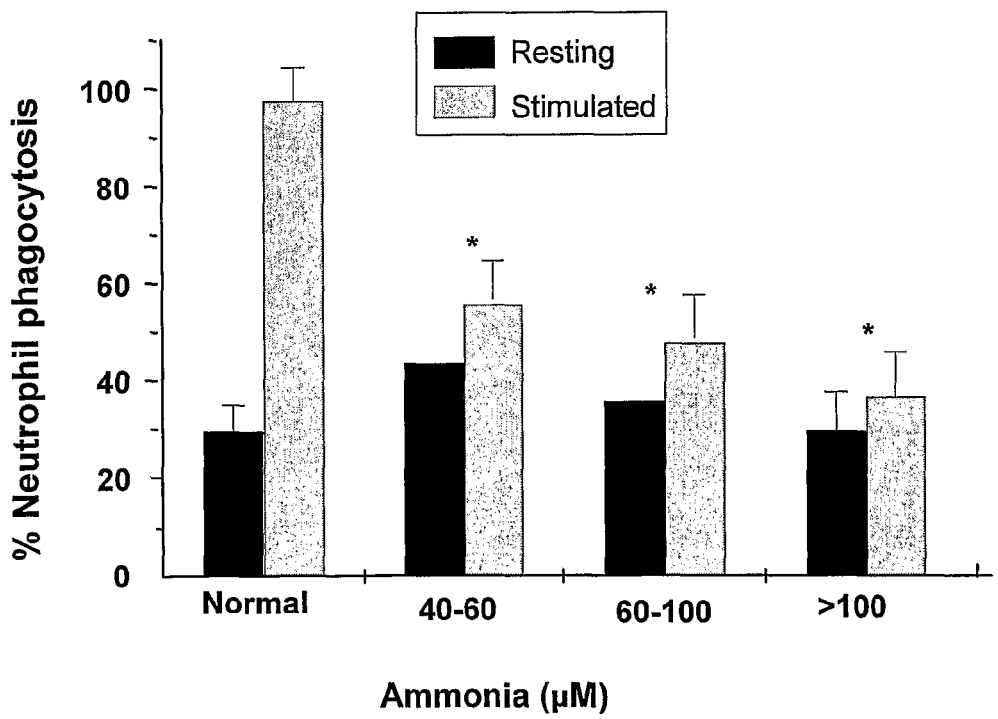
FIG. 2 shows that ammonia reduces neutrophil phagocytosis.
Figure 3:
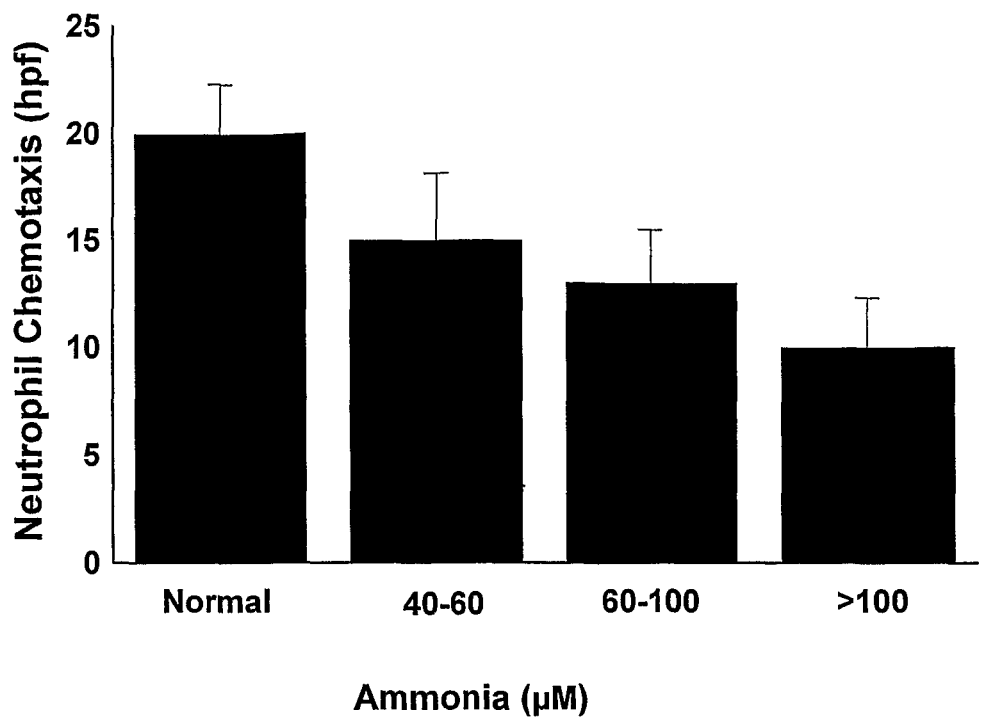
FIG. 3 shows that ammonia reduces neutrophil chemotaxis.

With incubation of increasing concentrations of ammonia, there was a significant reduction in neutrophil phagocytosis (FIG. 2) and also in neutrophil chemotaxis (FIG. 3).

EXAMPLE 3

The Effect of Ammonia on Neutrophil Phagocytosis can be Reversed by Interventions Methods for Measurement of Neutrophil Phagocytosis and Oxidative Burst As in Example 1.

Patients and Methods

Blood was collected from healthy volunteers (n=15) and incubated for 1 hour with ammonia and selected amino acids. The ability of the neutrophils to phagocytose bacteria was measured using the Phagotest assay.

Results

Figure 4:
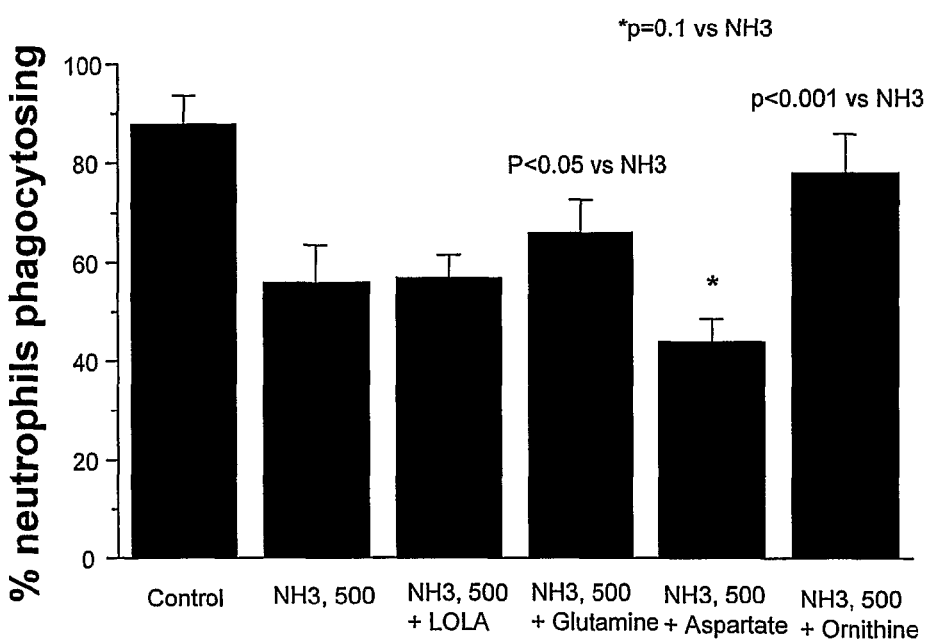
FIG. 4 shows that the effect of ammonia on neutrophil phagocytosis can be reversed by interventions.

We observed that the ammonia-induced reduction in neutrophil phagocytosis could be partially reversed by ornithine and glutamine (FIG. 4). However, neutrophil phagocytosis was made worse by co-incubation of ammonia with aspartate, but remained unchanged with L-ornithine L-aspartate.

EXAMPLE 4

A Simulated Gastrointestinal Bleed Reduces Neutrophil Chemotaxis which can be Partially Reversed by Administration of Isoleucine Methods Ten overnight fasted, metabolically stable patients with biopsy proven cirrhosis of the liver [9 males and 1 female; mean 49.6 years (SEM 9.1); mean Child-Pugh score of 7.8 (SEM 1.2)] were studied prior to and two hours after an oral administration of 75 grams of an amino acid mixture that mimics the hemoglobin molecule (Nutricia, Cuijk, Netherlands). In seven other patients [4 male and 3 female; mean 51.4 years (SEM 6.7); mean Child-Pugh score of 8.1 (SEM 1.4)], following administration of the amino acid mixture, isoleucine was administered intravenously over a 2 hour period (iso-osmotic solution containing 40 mg/l of isoleucine at a rate of 100 ml/hr). Neutrophil chemotaxis (see Example 1 for method) and plasma ammonia were measured in peripheral venous blood samples.

Results

Figure 5:
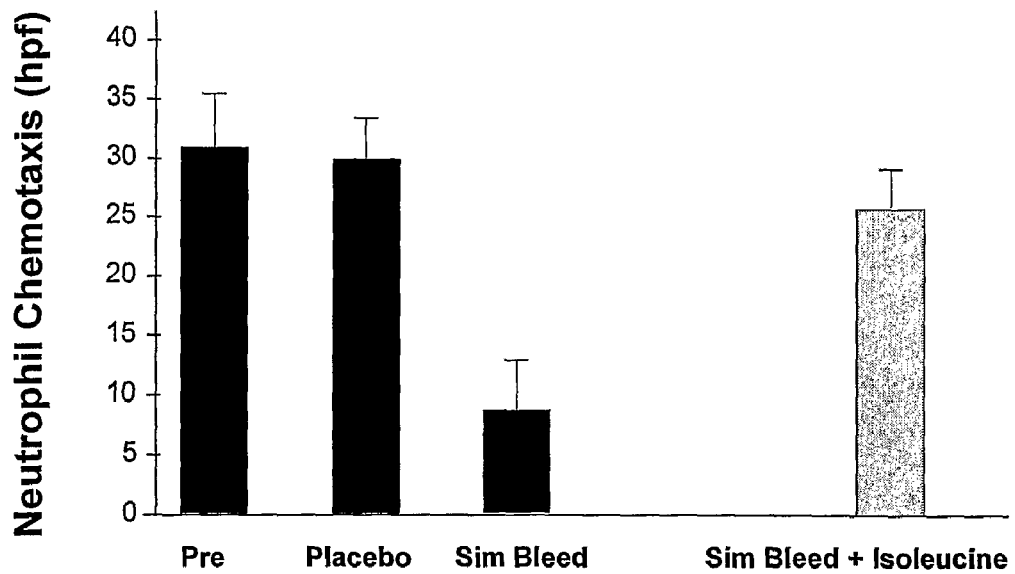
FIG. 5 shows that a simulated gastrointestinal bleed reduces neutrophil chemotaxis which can be partially reversed by administration of isoleucine.

Neutrophil chemotaxis was significantly lower in these cirrhotic patients compared with age-matched controls (53.3 SEM 4.6) and was significantly reduced after simulated bleeding from 31 (±4.2) to 8 (±5.4) cells/high power field (p<0.0001) (FIG. 5). Plasma concentration of ammonia increased significantly from 75.1 (±4.2) to 124 (±8.5) (p<0.001). The change in the concentration of ammonia correlated with the change in neutrophil chemotaxis (r=0.65 and p<0.05). The reduction in neutrophil chemotaxis observed with the simulated bleed was abrogated in the group of patients treated with isoleucine 25.4 (±6.0) cells/high power field.

EXAMPLE 5

A Simulated Bleed Reduces Protein Synthesis and Stimulates Isoleucine Oxidation Inappropriately Methods Five overnight fasted patients with cirrhosis of the liver were recruited. A blood sample was collected and expired air was sampled before the start of the infusion of the stable isotopes for the measurement of background isotope enrichment. Then the patients received a primed continuous intravenous infusion of $[1-^{13}C]$-isoleucine (1 mg/kg bw/h) until the end of the experiment (t=480 min).

Results

Figure 6:
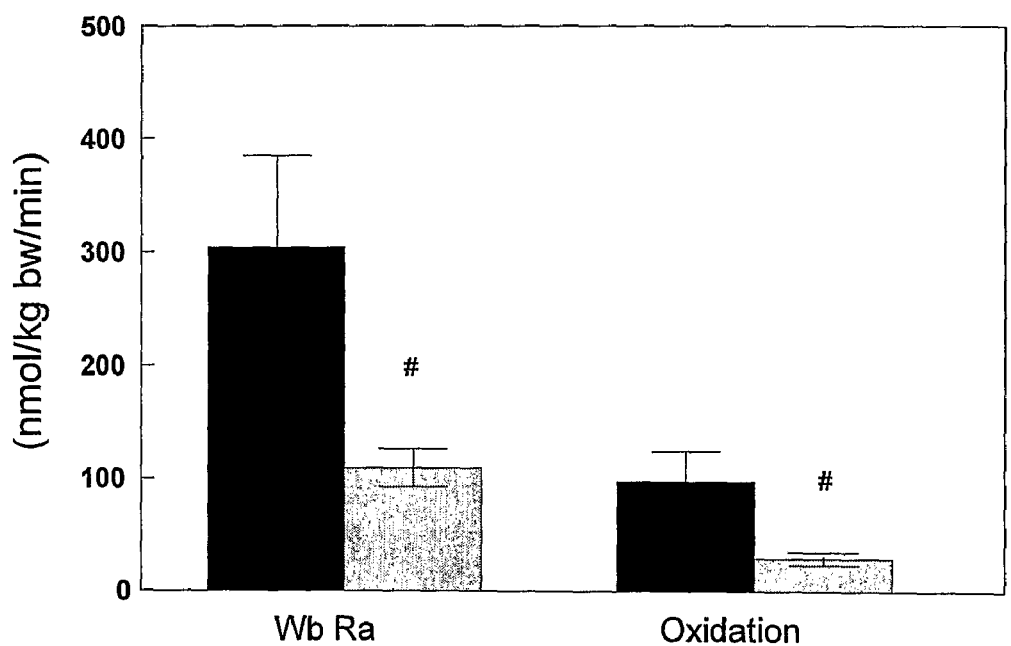
FIG. 6 shows that a simulated bleed reduces protein synthesis and stimulates isoleucine oxidation inappropriately.

FIG. 6 shows average whole body rate of appearance of isoleucine (Wb Ra) and isoleucine oxidation during the last hour of saline (black bars) and amino acid (grey bars) infusion (values in mean±SEM; # represents p<0.05). An upper GI bleed in patients with cirrhosis resulted in a reduction in isoleucine and markedly decreased whole body protein synthesis. The fraction of isoleucine flux used for oxidation did not change after the simulated bleed despite the marked reduction in isoleucine concentration, pointing to occurrence of BCAA antagonism.

EXAMPLE 6

Administration of Isoleucine During a Simulated Bleed Enhances Protein Synthesis but Does Not Reduce Ammonia Concentration Methods Sixteen metabolically stable patients with biopsy-proven cirrhosis of the liver were studied. Patients were randomized either to supplementation with isoleucine (40 mg/L solution; 50 ml/hr) or placebo during a simulated bleed over a 4-hour period. Protein synthesis (measured using primed continuous infusion of L-[ring-$^2H_5$]phenylalanine), L-[ring-$^2H_4$]tyrosine and L-[ring-$^2H_2$]tyrosine) and ammonia.

Results

Figure 7:
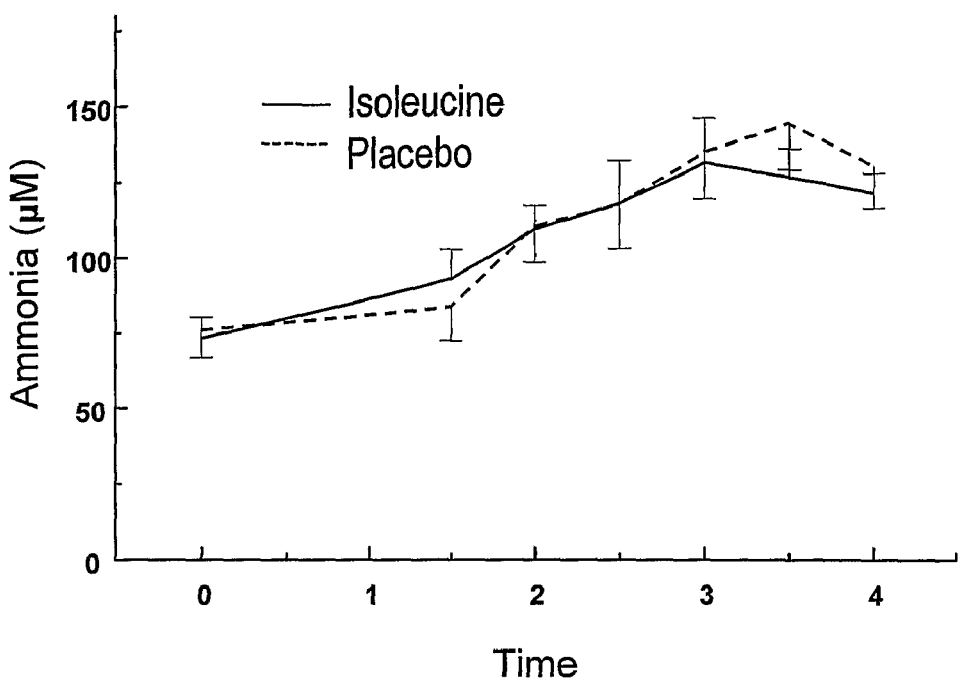
FIG. 7 shows that administration of isoleucine during a simulated bleed enhances protein synthesis but does not reduce ammonia concentration.

The results showed that infusion of isoleucine during a simulated bleed in patients with cirrhosis of the liver restores impaired protein synthesis of liver and muscle leading to a net anabolic state in these organs (Table 1). Ammonia concentration increased significantly in both groups but was not significantly different between those administered with isoleucine or placebo (FIG. 7).

EXAMPLE 7

Aspartate Accumulation Following Infusion of L-ornithine L-aspartate in Patients With Advanced Cirrhosis Methods 5 patients with advanced cirrhosis who were awaiting liver transplantation (age: 59; 3 male, Child Class C disease, severe ascites, creatinine 102 umol/L) were undergoing treatment with 40 g/day of L-ornithine L-aspartate.

Results

Over a 3 day period there was a significant and progressive increase in the aspartate concentration increasing to 5 times the basal value (Table 2).

TABLE 2

|  | PRE | Day 1 | Day 2 | Day 3 |
|---|---|---|---|---|
| ASPARTATE (µmol/L)) | 72 (11.8) | 178 (23.2) | 289 (27.1) | 354 (31.1) |

TABLE 1

Protein kinetics determined using the Phe model at t = 0 hours and at study end

|  |  | Time | Protein synthesis | P | Protein breakdown | P | Net Balance | P |
|---|---|---|---|---|---|---|---|---|
| Liver | SB-saline | 0 | 415 ± 120 |  | 263 ± 50 |  | 152 ± 76 |  |
|  |  | End | 274 ± 250 | 0.445 | 108 ± 162 | 0.366 | 166 ± 231 | 0.836 |
|  | SB-isoleucine | 0 | 218 ± 37 |  | 109 ± 25 |  | 98 ± 33 |  |
|  |  | End | 839 ± 221 | 0.038 | 157 ± 204 | 0.412 | 682 ± 165 | 0.010 |
| Leg | SB-saline | 0 | 117 ± 52 |  | 137 ± 51 |  | −20 ± 19 |  |
|  |  | End | 372 ± 211 | 0.189 | 288 ± 175 | 0.232 | 87 ± 140 | 0.694 |
|  | SB-isoleucine | 0 | −31 ± 201 |  | 196 ± 61 |  | −185 ± 152 |  |
|  |  | End | 377 ± 135 | 0.209 | 159 ± 100 | 0.535 | 261 ± 102 | 0.005 |

Data are mean ± SEM in nmol/kg body cell mass/min. End values represent the mean values of the final hour of the amino acid infusion. Protein synthesis data of liver and kidney are corrected for hydroxylation (see methods). Statistics: p values for Mann-Whitney U test for differences within groups; no significant differences were found between groups

EXAMPLE 8

Administration with LOLA Reduces Ammonia Concentration but Allows Ammonia to Regenerate Patients and Methods Eight patients with cirrhosis (age 56 (5.6), 5M, ALD-6; Grade 2 HE: 4; Grade 3-4 HE: 4) were treated with an infusion of LOLA (40 g over 8 hours). Blood was sampled for the measurement of ammonia and glutamine.

Results

Figure 8:
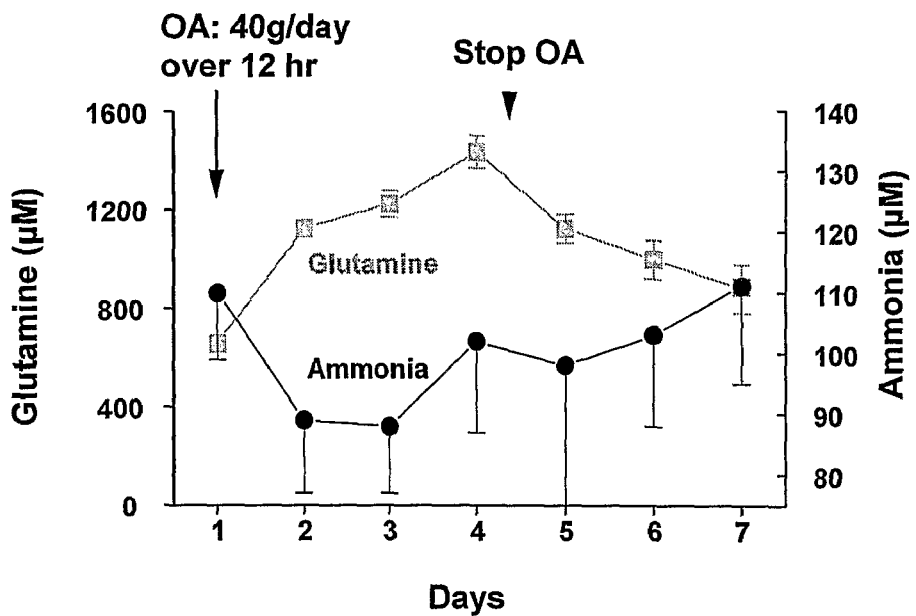
FIG. 8 shows that administration with LOLA reduces ammonia concentration but allows ammonia to regenerate.

The results showed that administration of LOLA resulted in a significant reduction in ammonia concentration with a concomitant rise in glutamine concentration (FIG. 8). This reduction in ammonia had beneficial effects upon the severity of HE. However, when LOLA was stopped, there was a rebound increase in the circulating ammonia levels, resulting in recurrence of HE in 3 of the 6 patients that had improved.

EXAMPLE 9

Active Removal of Glutamine Prevents the Secondary Rise in Ammonia Concentration Patients and Methods 3 patients (age 45 (4.1) 2M, ALD, all HE grade 3, HRS all 3) that were undergoing heamofiltration (CVVH) were treated with an infusion of LOLA (40 g over 8 hours). Blood was sampled for the measurement of ammonia and glutamine.

Results

Figure 9:
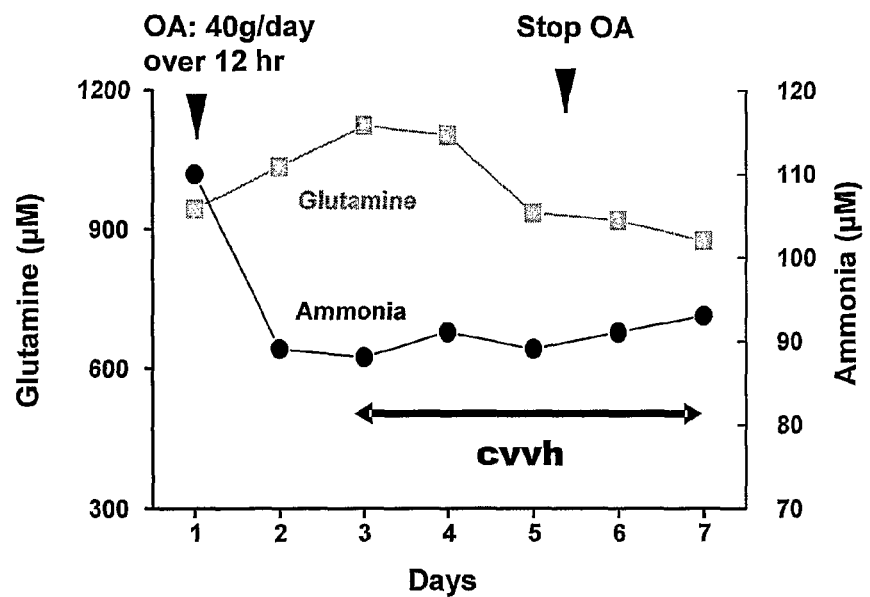
FIG. 9 shows that active removal of glutamine prevents the secondary rise in ammonia concentration.

The results showed that LOLA resulted in a reduction in ammonia concentration but the addition of dialysis prevented the concomitant increase in glutamine concentration (FIG. 9). Therefore, we believe there was a sustained reduction in ammonia concentration.

EXAMPLE 10

Phenylacetate Binds Glutamine to Make an Excretable Compound and Prevents the Secondary Rise in Ammonia Patients and Methods 6 patients with acute liver failure (5 non-A non-B Hepatitis) and severe encephalopathy (Grade 3-4) were treated with LOLA and phenylacetate (40 g/day over 8 hours).

Results

Figure 10:
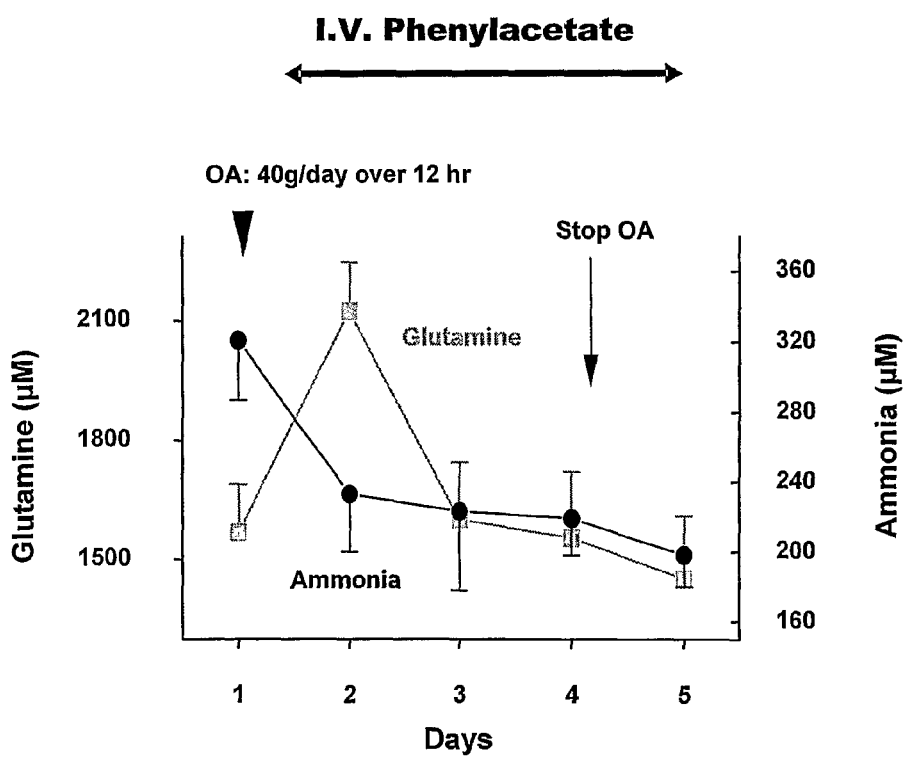
FIG. 10 shows that phenylacetate binds glutamine to make an excretable compound and prevents the secondary rise in ammonia.

There was no significant increase in glutamine concentration and ammonia levels were reduced with the combined treatment (FIG. 10). No rebound increase in ammonia was observed.

EXAMPLE 11

The Effect of Ornithine and Phenylbutyrate in Human Patients with Hepatic Encephalopathy Patients 1. Groups—3 patients per group. Total 12.
2. Inclusion Criteria
    adult patients aged 18-80 years,—liver cirrhosis documented by histology or clinical criteria
    HE type C,—ammonia concentration of >80 umol/L, informed consent/assent
3. Exclusion Criteria
    other concomitant neurological disorder,—use of another specific ammonia lowering drug,—respiratory failure requiring mechanical ventilation and sedation,—uncontrolled gastrointestinal bleeding,—hypotension requiring inotropes, overt renal failure (creatinine >2 mg/dl), hemodialysis,—extracorporeal liver support, known hypersensitivity to any of the study drugs,—pregnancy.

Assessment of Mental State

Grading of Hepatic Encephalopathy (West Haven Criteria)

| | |
|---|---|
| Grade 0 (minimal HE) | normal mental state (one or more quantifiable abnormalities on psychometric testing) |
| Grade 1 | trivial lack of awareness euphoria or anxiety shortened attention span impaired performance of addition |
| Grade 2 | lethargy or apathy minimal disorientation for time or place subtle personality change inappropriate behaviour impaired performance of subtraction |
| Grade 3 | somnolence to semi-stupor, but responsive to verbal stimuli confusion gross disorientation |
| Grade 4 | coma (unresponsive to verbal or noxious stimuli) |

Methods

In an open labelled study, we included 8 patients with cirrhosis and hyperammonemia. They were matched for the severity of liver disease (see Table 3). They were treated with one of the following regimes for a 3 day period and observations were made for 5 days. The study groups were:

(i) Placebo: 5% Dextrose over 4 hours;

(ii) Ornithine alone: 20 g in 500 ml, 5% dextrose between 0800 and 1200;

(iii) Phenylbutyrate: 10 g twice daily, orally (0800 and 1600); and (iv) Ornithine+Phenylbutyrate: 20 g in 500 ml, 5% dextrose between 0800 and 1200+10 g twice daily, orally (0800 and 1600).

Patients were fasted overnight between 0000 midnight and 0800 am. They were fed intragastrically with a diet of 25 KCal/Kg that included 1 g/Kg protein diet starting at 0800 and finishing at midnight. Blood was sampled at 0730 am and then at 1800 hr for the measurement of ammonia and glutamine. Patients were monitored closely for side effects. The drug was tolerated well in each of the groups and no adverse events were observed.

TABLE 3

Patient Demographics

| | Placebo | Ornithine alone | Phenylbutyrate alone | OP |
|---|---|---|---|---|
| Age | P1: 47 | P3: 46 | P5: 56 | P7: 52 |
| | P2: 57 | P4: 40 | P6: 48 | P8: 52 |
| Sex | P1: M | P3: F | P5: F | P7: M |
| | P2: M | P4: F | P6: M | P8: F |
| Aetiology of Liver Disease | P1: HCV P2: HBV | P3: HBV P4: NASH | P5: NASH P6: HBV | P7: HBV P8: HBV |
| Severity of Liver Disease (Pugh Score) | P1: 9 P2: 12 | P3: 13 P4: 13 | P5: 14 P6: 13 | P7: 14 P8: 12 |
| Precipitating Factor | P1: Infection P2: Infection | P3: SBP P4: Infection | P5: SBP P6: ?infection | P7: SBP P8: Infection |
| Severity of HE (West-Haven criteria) | P1: 2 P2: 3 | P3: 3 P4: 3 | P5: 3 P6: 3 | P7: 3 P8: 3 |
| Severity of HE (Glasgow coma score) | P1: 9 P2: 8 | P3: 8 P4: 8 | P5: 9 P6: 10 | P7: 9 P8: 9 |
| Other organ failure | P1: none P2: hypotension | P3: pre-renal, hypotension P4: hypotension | P5: none P6: pre-renal | P7: none P8: none |
| Dead/Alive | P1: A P2: A | P3: D P4: A | P5: A P6: A | P7: A P8: A |
| Complications | P1: infection, SBP P2: infection, variceal bleed | P3: HRS P4: rec. infection | P5: sepsis, ICU P6: recurrent SBP | P7: none P8: bleed, day 14 |

Figure 11:
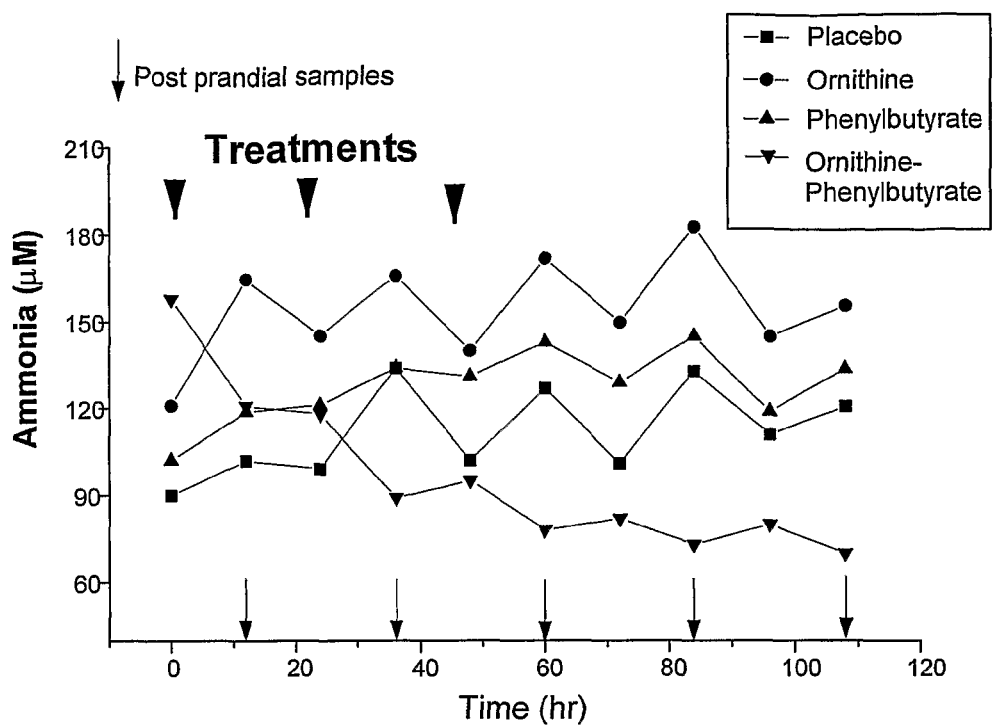
FIG. 11 shows the effect of ornithine and phenylbutyrate on ammonia levels in patients with advanced cirrhosis.

SBP: spontaneous bacterial peritonitis, Non alcoholic steatohepatitis,
ICU: Intensive care support needed,
HRS: hepatorenal syndrome Results FIG. 11 shows that the mean ammonia levels remained largely unchanged over the period of treatment in the placebo group. In the L-Ornithine and the Phenylbutyrate group, the ammonia concentration increased from baseline values. In the group treated with both L-ornithine and Phenylbutyrate, there was a substantial reduction of ammonia. The postprandial increase in ammonia was reduced in the OP treated animals in addition to the reduction in ammonia concentrations. Both patients in the OP group had improved their encephalopathy score by 2 grades by day 3, which was not observed in any of the other 6 patients.

Figure 12:
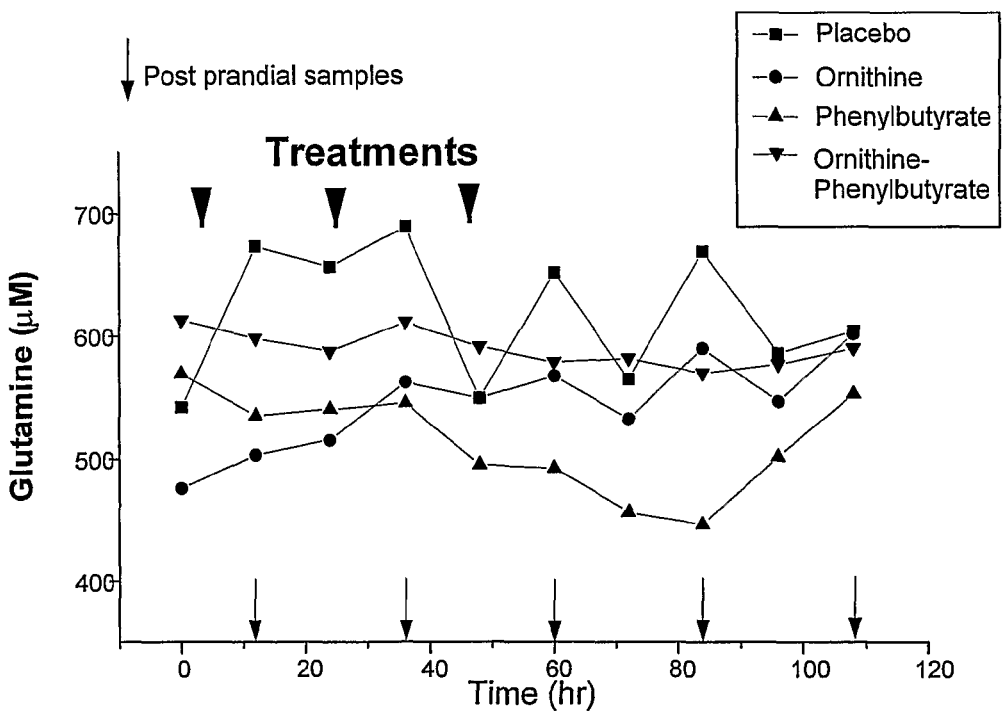
FIG. 12 shows the effect of ornithine and phenylbutyrate on glutamine levels in patients with advanced cirrhosis.

FIG. 12 shows that the mean glutamine levels remained largely unchanged over the period of treatment in the OP group despite a reduction in ammonia. There was a reduction in glutamine in the Phenylbutyrate group, which may well be deleterious. In the L-Ornithine and placebo groups there was an increase in Glutamine concentrations which was markedly accentuated in the postprandial state.

Figure 13:
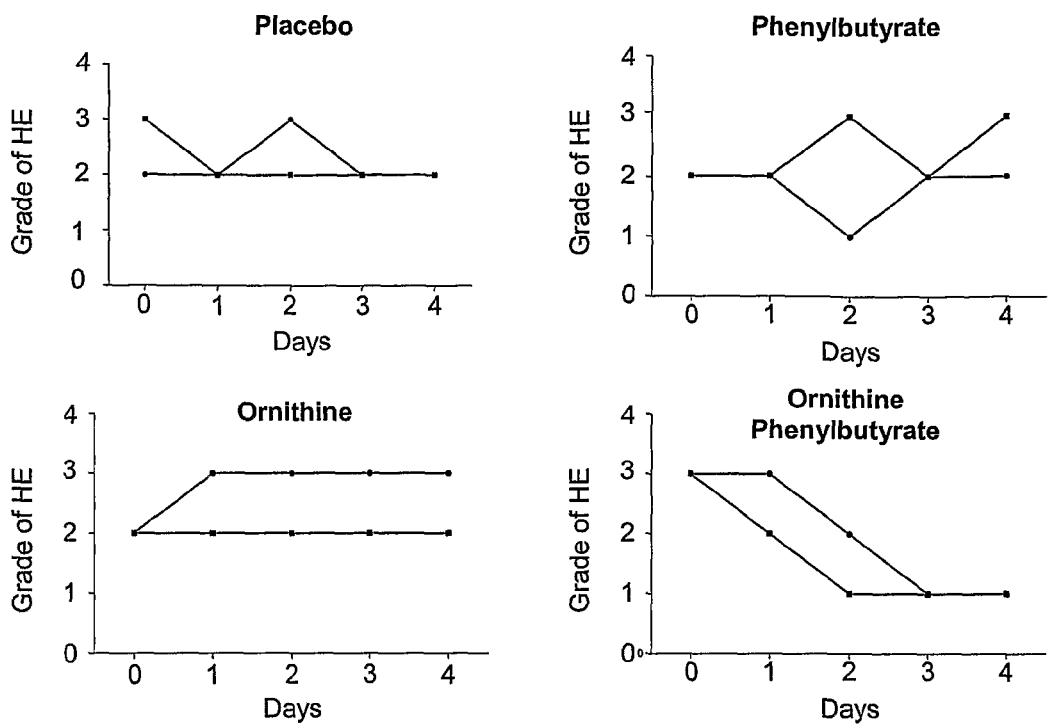
FIG. 13 shows the changes in mental state of patients treated with placebo, O, P or O+P.

FIG. 13 shows the changes in mental state in the groups treated with Placebo, O, P and OP.

EXAMPLE 12

The Effect of Ornithine, Phenylbutyrate and Isoleucine in Human Patients with Hepatic Encephalopathy Patients
1. Groups—2 patients per group. Total 6
2. Inclusion Criteria Adult patients aged 18-80 years, liver cirrhosis documented by histology or clinical criteria, Child B or C, recent Gastrointestinal bleed from varices (<6 hours after presentation), informed consent/assent.

3. Exclusion Criteria other concomitant neurological disorder, use of another specific ammonia lowering drug, respiratory failure requiring mechanical ventilation and sedation, uncontrolled gastrointestinal bleeding, hypotension requiring inotropes, overt renal failure (creatinine >2 mg/dl), hemodialysis, extracorporeal liver support, known hypersensitivity to any of the study drugs, pregnancy/lactation.

Methods

In an open labelled study, we included 6 patients with cirrhosis and who were admitted for management of variceal bleeding. They were matched for the severity of liver disease (see Table 4). They were treated with one of the following regimes for a 3 day period and observations were made for 5 days. The study groups were:

i. Placebo: 5% Dextrose over 4 hours (250 ml)
  ii. Isoleucine alone: 10 gm IV in 250 ml 5% Dextrose over 2 hours in two divided doses.
  iii. Isoleucine+Ornithine+Phenylbutyrate: Isoleucine: 10 gm IV in 250 ml 5% Dextrose over 2 hours in two divided doses; Ornithine: 20 g in 250 ml, 5% Dextrose (t=0; 24, 48 hr); Phenylbutyrate: 10 g twice daily, orally (t=0, 12, 24, 36, 48 hr).

Patients were fasted overnight between 0000 midnight and 0800 am. They were fed intragastrically with a diet of 25 KCal/Kg that included 1 g/Kg protein diet starting at 0800 and finishing at midnight. Blood was sampled at 0730 am and then at 1800 hr for the measurement of ammonia and glutamine. Patients were monitored closely for side effects. The drug was tolerated well in each of the groups and no adverse events were observed. Because the patients received sedation for their initial endoscopy, the mental state assessment was impossible to interpret. One patient each in the Placebo and the Isoelucine groups died from multiorgan failure in the hospital. The rest of the patients survived.

TABLE 4

|  | Placebo | Isoleucine alone | OIP |
|---|---|---|---|
| Age | P1: 43 | P3: 57 | P5: 43 |
|  | P2: 62 | P4: 42 | P6: 45 |
| Sex | P1: M | P3: F | P5: M |
|  | P2: M | P4: M | P6: M |
| Aetiology of Liver Disease | P1: ALD | P3: HBV | P5: HBV |
|  | P2: HCV | P4: ALD | P6: NASH |
| Severity of Liver Disease (Pugh Score) | P1: 13 | P3: 13 | P5: 14 |
|  | P2: 14 | P4: 11 | P6: 10 |
| Severity of HE (West-Haven criteria) | P1: 2 | P3: 2 | P5: 2 |
|  | P2: 3 | P4: 1 | P6: 2 |
| Estimated Blood Loss (u) | P1: 9 | P3: 7 | P5: 7 |
|  | P2: 10 | P4: 8 | P6: 10 |
| Dead/Alive | P1: D | P3: A | P5: A |
|  | P2: A | P4: D | P6: A |
| Complications | P1: infection, rebleed | P3: HRS | P5: chest infection |
|  | P2: severe encephalopathy | P4: rec. infection | P6: none |

Figure 14:
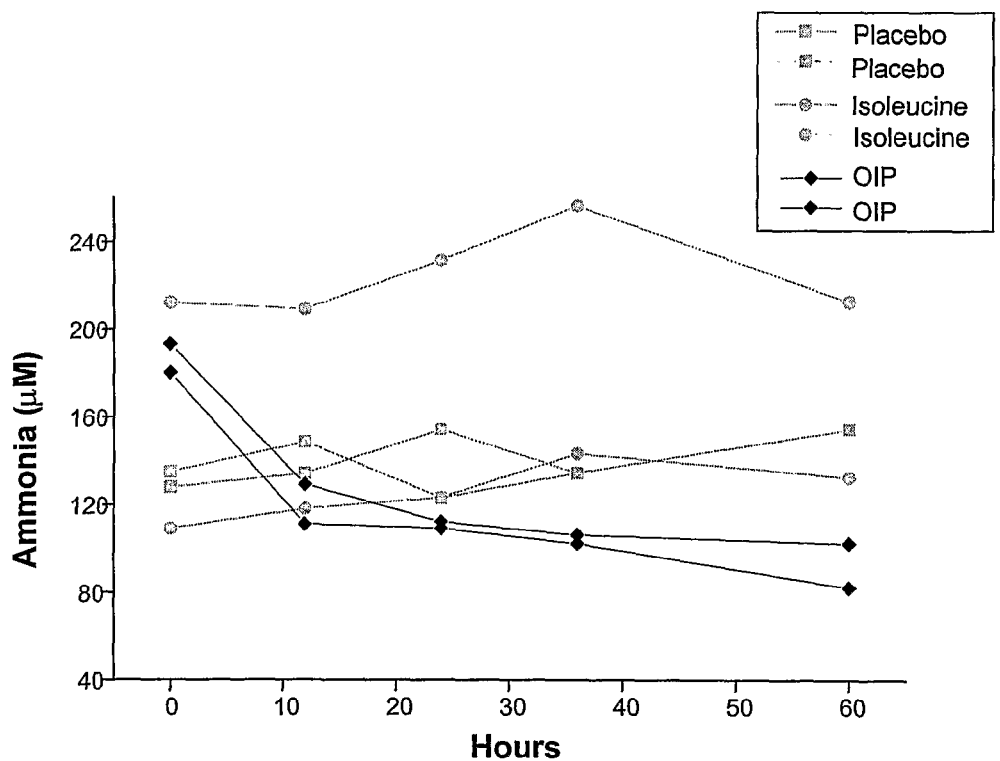
FIG. 14 shows the effect of ornithine, phenylbutyrate and isoleucine on ammonia levels in patients with advanced cirrhosis.

SBP: spontaneous bacterial peritonitis, Non alcoholic steatohepatitis,
ICU: Intensive care support needed,
HRS: hepatorenal syndrome Results FIG. 14 shows that no significant changes in ammonia concentrations in the placebo and the Isoleucine groups. In the group treated with OIP, there was a substantial reduction in ammonia concentration.

Figure 15:
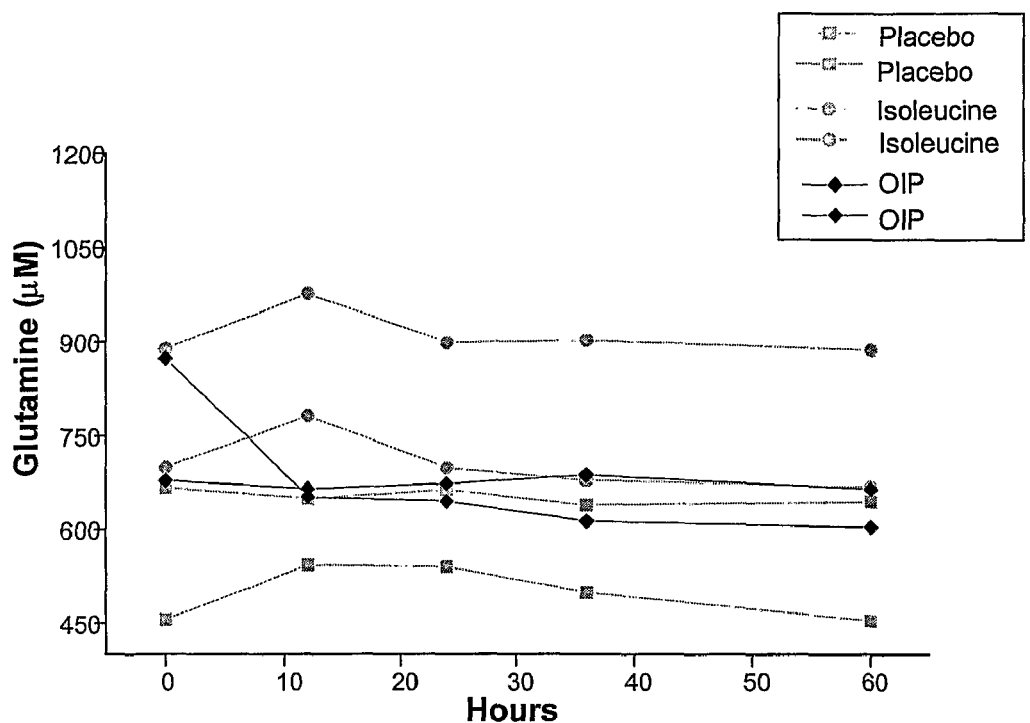
FIG. 15 shows the effect of ornithine, phenylbutyrate and isoleucine on glutamine levels in patients with advanced cirrhosis.

FIG. 15 shows that the glutamine levels are not significantly altered by administration of either Isoleucine, Placebo or OIP. Only in the OIP group the ammonia was reduced substantially.

Figure 16:
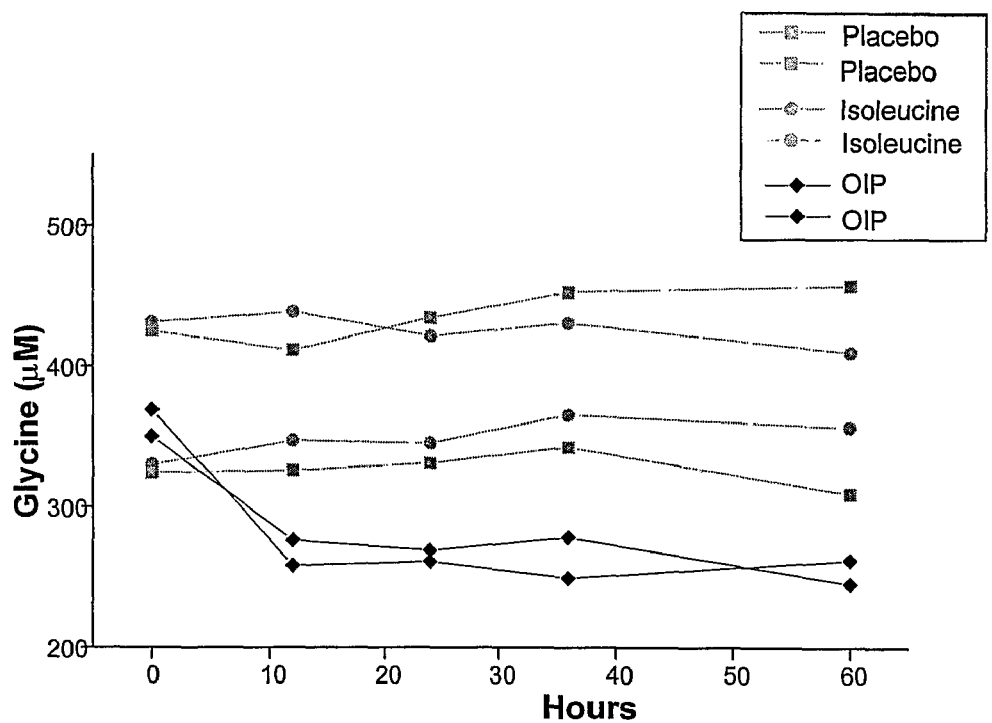
FIG. 16 shows the effect of ornithine, phenylbutyrate and isoleucine on glycine levels in patients with advanced cirrhosis.

FIG. 16 shows an alternative by which OIP may act is through a reduction in the ammoniagenic amino acid, Glycine. Substantial reduction in Glycine is observed only in the OIP group.

Figure 17:
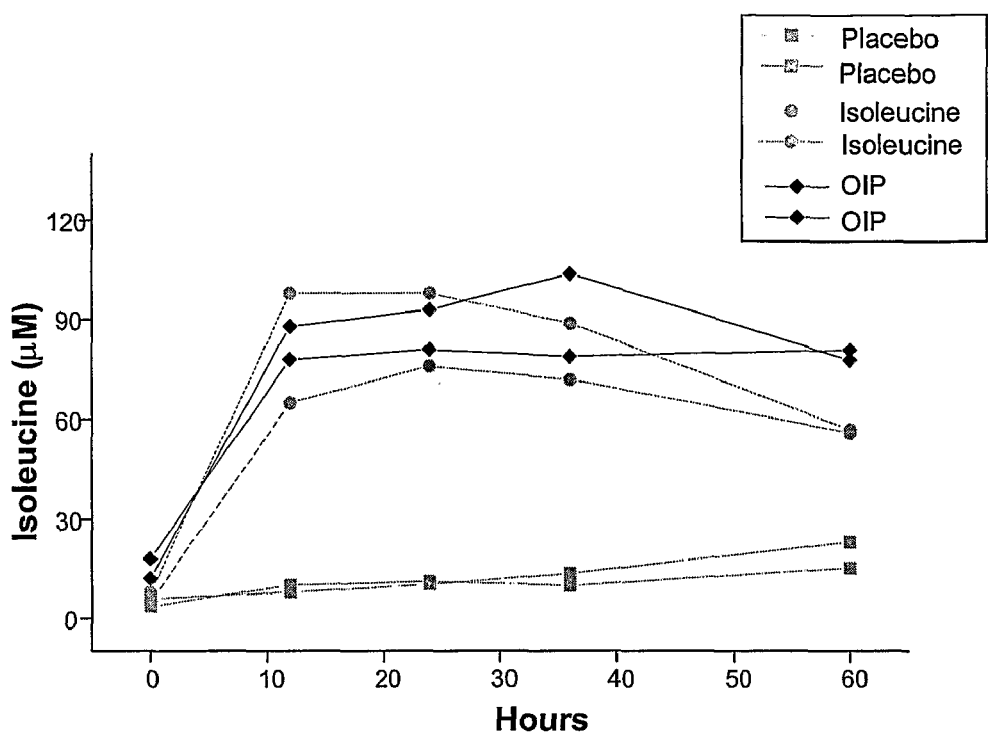
FIG. 17 shows the effect of ornithine, phenylbutyrate and isoleucine on isoleucine levels in patients with advanced cirrhosis.

FIG. 17 shows the isoleucine levels are very low to start with in each of the groups but increases to twice normal values in the Isoleucine treated groups. The concentration in the Placebo group remains low and unchanged.

Figure 18:
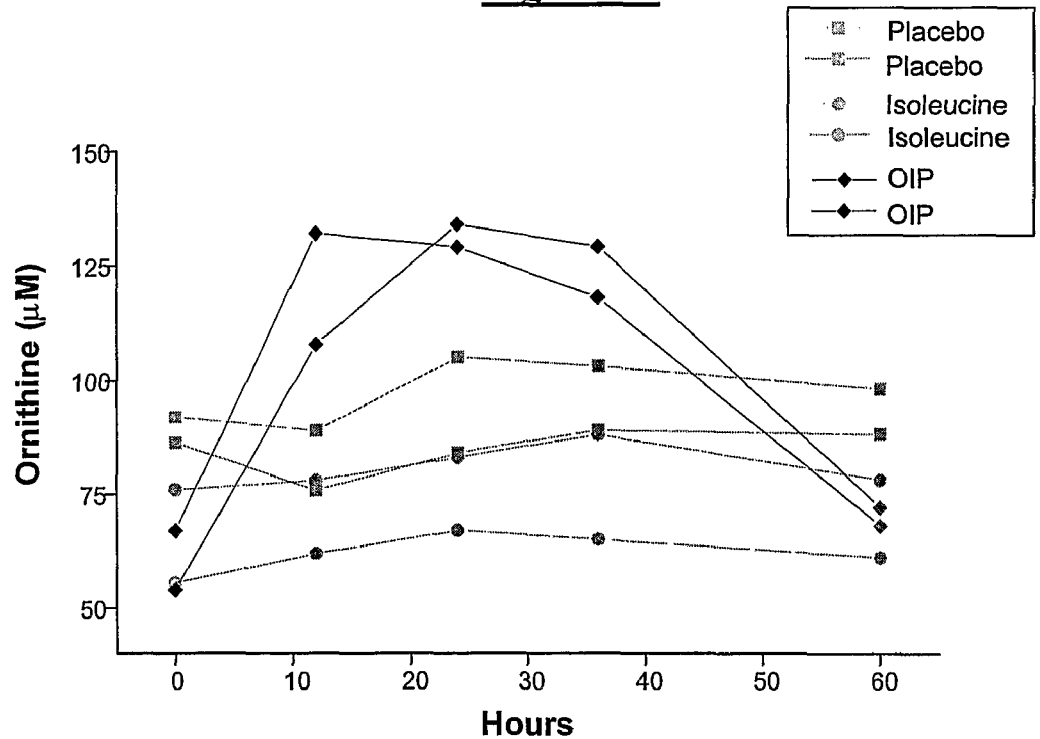
FIG. 18 shows the effect of ornithine, phenylbutyrate and isoleucine on ornithine levels in patients with advanced cirrhosis.

FIG. 18 shows the changes in the Ornithine levels in the patients over the course of treatment showing marked sustained increase in the concentrations of Ornithine which are significantly reduced to basal values on stopping the drug indicating uptake in the different tissues.

EXAMPLE 13

The Effect of Ornithine and Phenylbutyrate in the Bile Duct Ligated Rat

Methods

Induction of Cirrhosis by Bile Duct Ligation (BDL)

Male Sprague-Dawley rats (200-250 g) were used for this procedure. Following anaesthetisation, a mid-line laparotamy was performed, the bile duct was exposed, triply ligated with 4.0 silk suture, and severed between the second and third ligature. The wound was closed in layers with absorbable suture, and the animal allowed to recover in a quiet room before being returned to the animal storage facility. Animals were kept at a constant temperature (20° C.) in a 12 hour light/dark cycle with access to water and standard rodent chow ad libitum.

After five weeks post BDL (or sham procedure) the animals were switched from rodent chow to a complete liquid diet (Liquidiet, Bio-Serv, Frenchtown N.J., USA) to which was added an amino acid mixture mimicking the composition of haemoglobin (2.8 g/Kg/day, Nutricia Cuijk, The Netherlands, Product No. 24143). At six weeks, under anaesthesia a right carotid arterial catheter was inserted and used to collect repeated blood samples. Following this procedure a baseline sample was collected prior to administration of the study formulations by IP injection. The study groups were: BDL control+Saline (n=5), BDL+ornithine (0.22 g/Kg, n=6) in saline IP, BDL+phenylbutyrate (0.3 g/Kg, n=7) in saline IP, BDL+OP (0.22 g/Kg/0.3 g/Kg, n=7) in saline IP.

Blood samples were collected into pre-cooled heparinsed tubes and stored on ice prior to processing. Plasma was collected following centrifugation (3,000 rpm, 10 mins) and stored at −80° C. prior to analyses.

Ammonia, glucose, lactate and urea were measured using a COBAS Mira S according to manufacturers instructions. Amino acids were quantified by HPLC with fluorescence detection.

Results

In the cirrhotic bile duct ligated rat model there is a substantial increase in the arterial plasma ammonia level (205±11 µmoles/L, mean±SEM) compared with healthy controls (25.6±2 µmoles/L, $p<0.001$ data, not shown). In this model we found that there was no change in the arterial ammonia levels over three hours in the saline treated placebo group.

Figure 19:
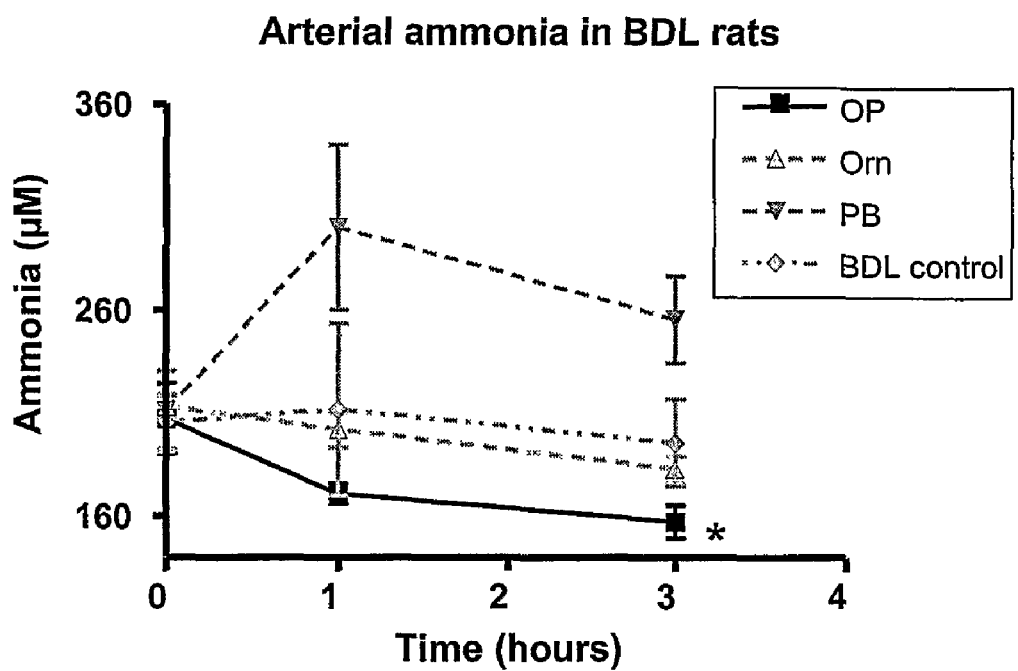
FIG. 19 shows the effect of ornithine and phenylbutyrate on arterial ammonia in the bile duct ligated rat model.

FIG. 19 shows the change in arterial plasma ammonia levels in BDL cirrhotic rats following IP injections of saline (BDL control, n=5), ornithine (Orn, 0.22 g/Kg, n=6), phenylbutyrate (PB, 0.3 g/Kg, n=7) and ornithine phenylbutyrate (OP, 0.22 g Kg+0.3 g/Kg, n=7). * signifies $p<0.05$ for OP vs Orn at 3 hours (2 way ANOVA).

This figure shows that in the ornithine treated animals a slight decrease in ammonia concentration was detected, though this was not found to be different from placebo. In the phenylbutyrate treated group a significant increase in plasma ammonia was found after 1 hour ($p<0.01$ vs all other groups), though this difference was found to be smaller at the three hour time point. This finding fits with the hypothesis that phenylbutyrate (phenylacetate) is only effective in subjects with raised glutamine concentrations. In the animals without ornithine supplementation which can be metabolised to form glutamine the effects of P alone are undesirable and are potentially harmful. A significantly lower ammonia level was observed in the ornithine plus phenylbutyrate (OP) treated group. In these animals a sustained lowering of ammonia was measured over the three hour duration of the study the levels of which were found to be significantly less than those in the ornithine only group at the end of the study ($p<0.05$).

This clearly demonstrates that the combination of OP has greater efficacy in reducing plasma ammonia than either O or P alone. Furthermore, the increased plasma levels of ammonia may be detrimental in the P alone treated animals.

Figure 20:
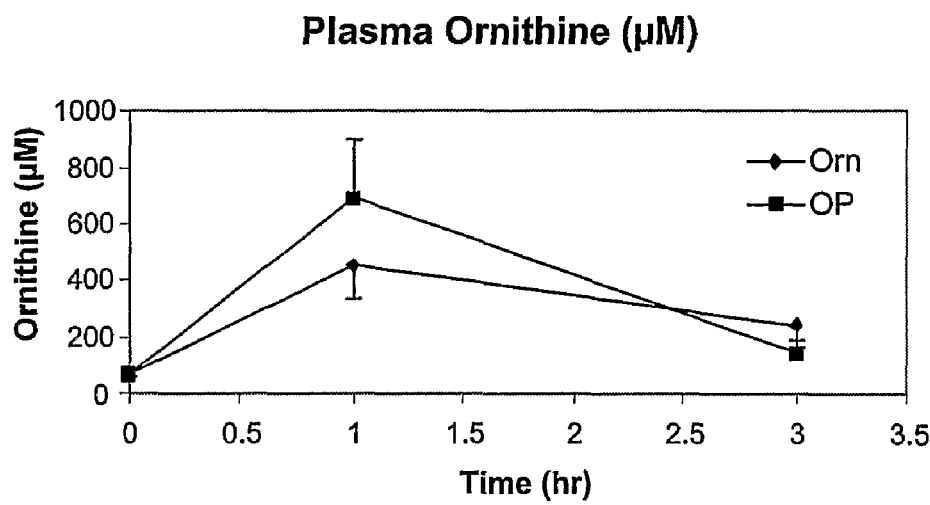
FIG. 20 shows the effect of ornithine and phenylbutyrate on plasma ornithine in the bile duct ligated rat model.

In a subset of samples we examined the uptake of ornithine into the blood stream following IP injection of O or OP. FIG. 20 shows the arterial ornithine concentration in the supplemented groups. It can be clearly seen that in both groups the plasma ornithine concentration is markedly increased at 1 hour following the IP injection, which is subsequently reduced at 3 hours as this ornithine is metabolised in the body. No significant difference was found in plasma ornithine concentration between these groups at any time point.

This finding is important as it demonstrates that the chosen method of administration is effective in delivering ornithine in these animals. Furthermore, the rapid uptake and observed decrease in plasma levels indicate that active metabolism of this amino acid is occurring.

EXAMPLE 14

The Effect of Ornithine, Phenylbutyrate and Isoleucine in the Bile Duct Ligated Rat Methods Male Sprague-Dawley rats (200-250 g) were used for this procedure. For the 48 hrs prior to sacrifice the animals were switched from standard rodent chow to a complete liquid diet (Liquidiet, Bio-Serv, Frenchtown N.J., USA) to which was added an amino acid mixture mimicking the composition of haemoglobin (2.8 g/Kg, Nutricia Cuijk, The Netherlands, Product No. 24143). Acute liver failure (ALF) was induced 24 hours prior to sacrifice by IP injection of galactosamine (1 g/Kg, Sigma, Poole UK) in saline (n=5 in each group). Three hours prior to sacrifice animals were treated with either a formulation of OIP (ornithine 0.22 g/Kg, isoleucine 0.25 g/Kg, phenylbutyrate 0.3 g/Kg, in saline IP) or saline control. At the termination of the experiment arterial blood was collected into pre-cooled heparinised tubes and stored on ice until processing. Plasma was collected and stored as above. Ammonia was determined as above.

Results

Figure 21:
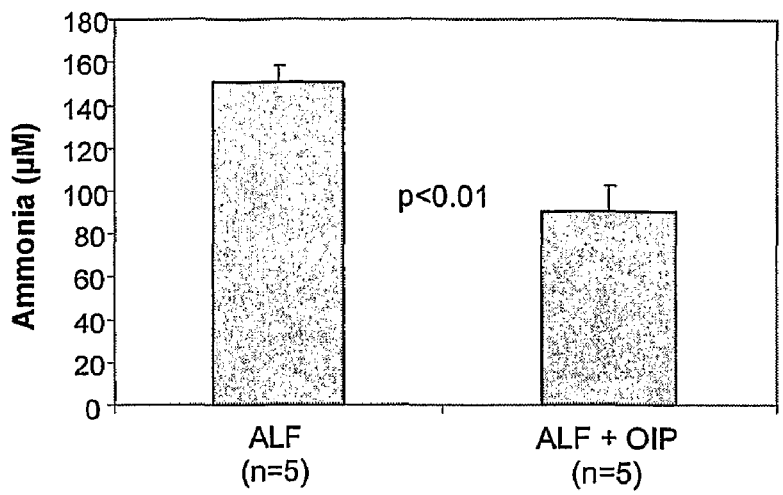
FIG. 21 shows the effect of ornithine, phenylbutyrate and isoleucine on arterial plasma ammonia levels in a hyperammonaemic acute liver failure rat model.

Arterial ammonia levels were found to be significantly reduced in acute liver failure rats treated with OIP compared with placebo controls (FIG. 21). This study was designed to test whether isoleucine in combination with ornithine and phenylbutyrate (phenylacetate) would be able to effectively lower plasma ammonia. It has been previously demonstrated that isoleucine alone does not effect ammonia levels in human studies, though its efficacy in combination with O and P has not been previously tested.

FIG. 21 shows arterial plasma ammonia levels in a hyperammonaemic acute liver failure model for saline placebo (ALF) and OIP treated (ALF+OIP). A significance level of $p<0.01$ was found between these two groups (T-Test).

This finding supports the hypothesis that isoleucine in combination with ornithine and phenylbutyrate is effective in reducing ammonia levels. These are in addition to the beneficial effects of isoleucine previously described for protein synthesis.

EXAMPLE 15

The Effect of Ornithine and Phenylbutyrate in the Devascularized Pig Model

Methods

Five pigs were randomised into four groups: acute liver failure (ALF)+placebo+placebo (n=2); ALF+Ornithine+placebo; ALF+Phenylbutyrate+placebo; ALF+Ornithine and Phenylbutyrate. Pigs had catheters inserted into the femoral artery and vein, portal vein, renal vein and pulmonary artery. The experiment started at time=−1 hr, when placebo or treatment infusions were started.

1. Placebo: 5% Dextrose over 3 hours, oral water placebo
2. Ornithine alone: 0.3 g/Kg, 5% dextrose over 3 hours intravascular drip
3. Phenylbutyrate: 0.3 g/Kg, 5% dextrose over 3 hours intragastric feed Ornithine+Phenylbutyrate: 0.3 g/Kg, 5% dextrose over 3 hours intravascular drip, 0.3 g/Kg, 5% dextrose over 3 hours intragastric feed.

ALF was induced by portal vein anastamosis to the inferior vena cava and subsequent hepatic artery ligation (devascularisation) at time=0 hr; infusions were stopped at t=+2 hr and the experiment was terminated at time=8 hr. Blood and urine samples were collected at time=0, 1, 3, 5, 7 and 9 hr for the measurement of regional ammonia and amino acid changes. At the end of the experiment a section of frontal cortex was removed for brain water measurements.

Results

Following ornithine infusion generating intracellular glutamate and the intragastric supply of conjugating phenylacetate results suggest profound alteration in overall ammonia levels and glutamine utilization in this catastrophic model of liver failure.

Figure 23:
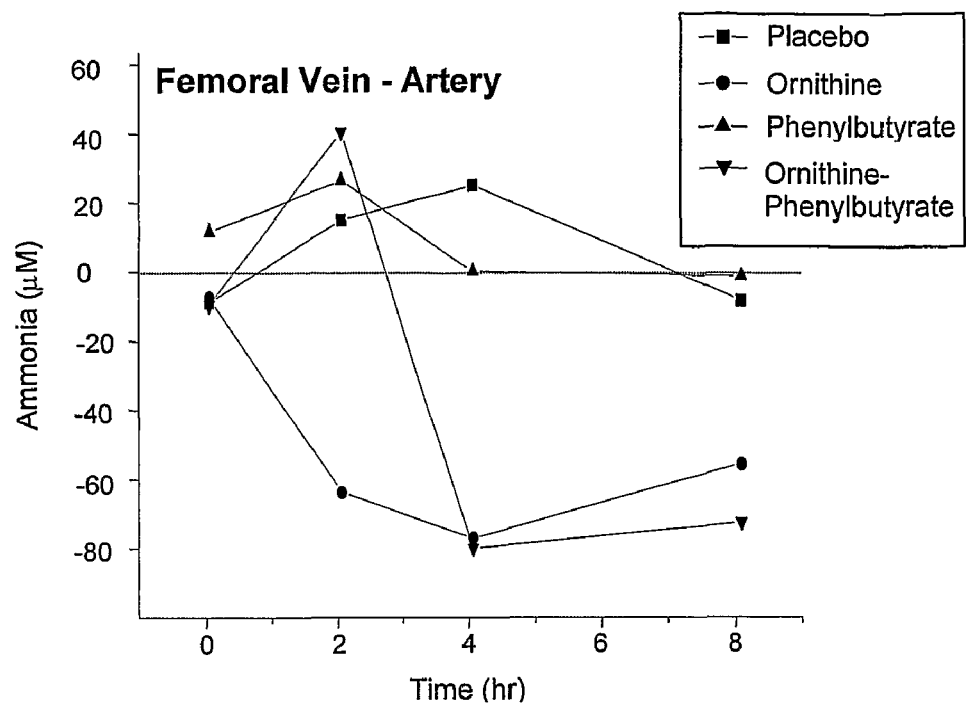
FIG. 23 shows that ammonia is being taken from the blood by the muscle in the O and the OP treated animals (samples were taken from the femoral vein-artery). In contrast, the placebo and the P alone animals shows an increase in ammonia production by the muscle.
Figure 24:
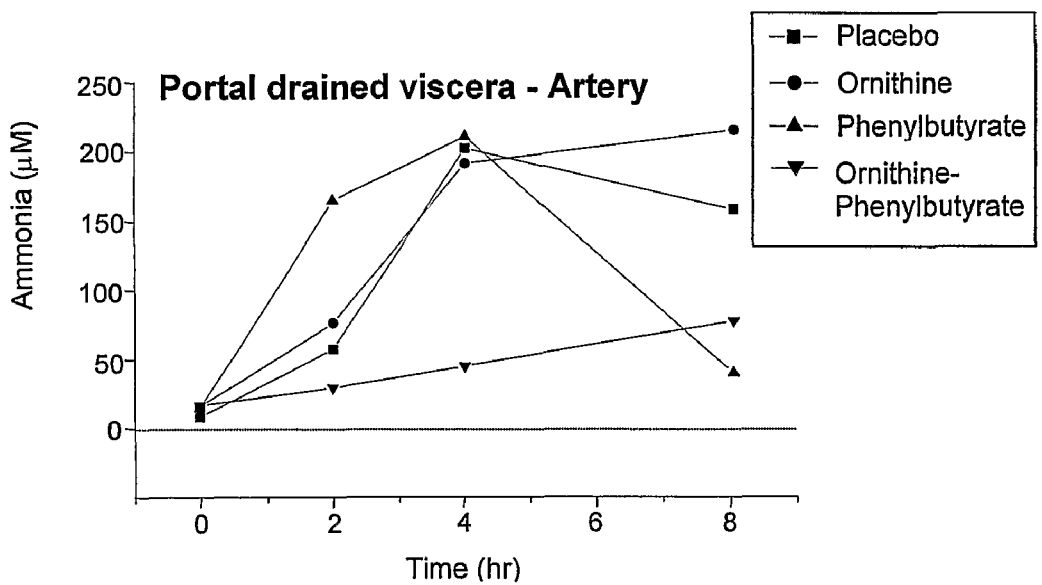
FIG. 24 shows that ammonia is produced by the gut in all animals except the OP treated animal (samples were taken from the portal drained viscera-artery).
Figure 25:
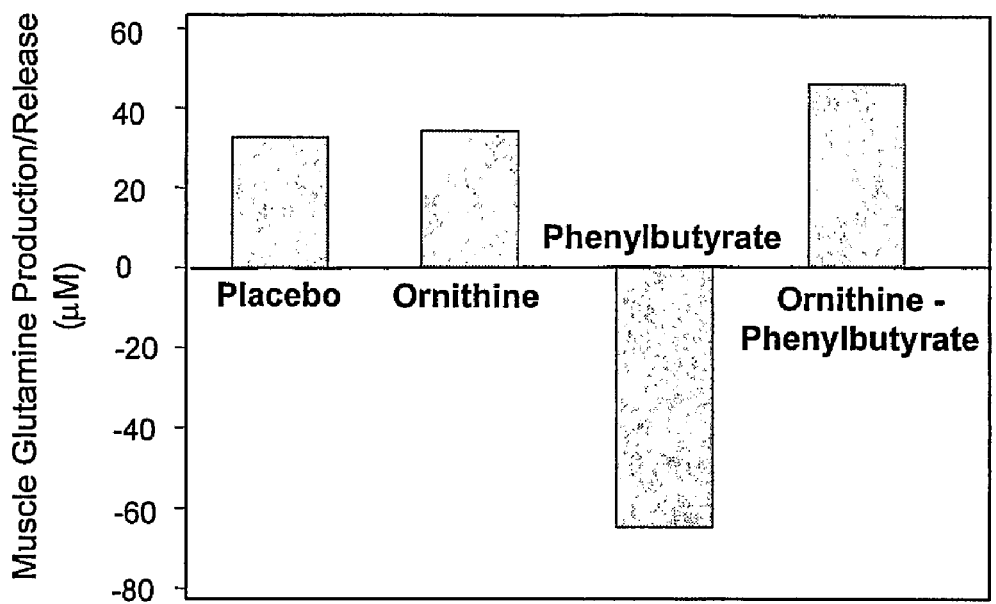
FIG. 25 shows that muscle glutamine release is increased by O but not P used in isolation. OP caused a markedly greater release of muscle glutamine (thereby trapping ammonia as glutamine in the muscle).
Figure 26:
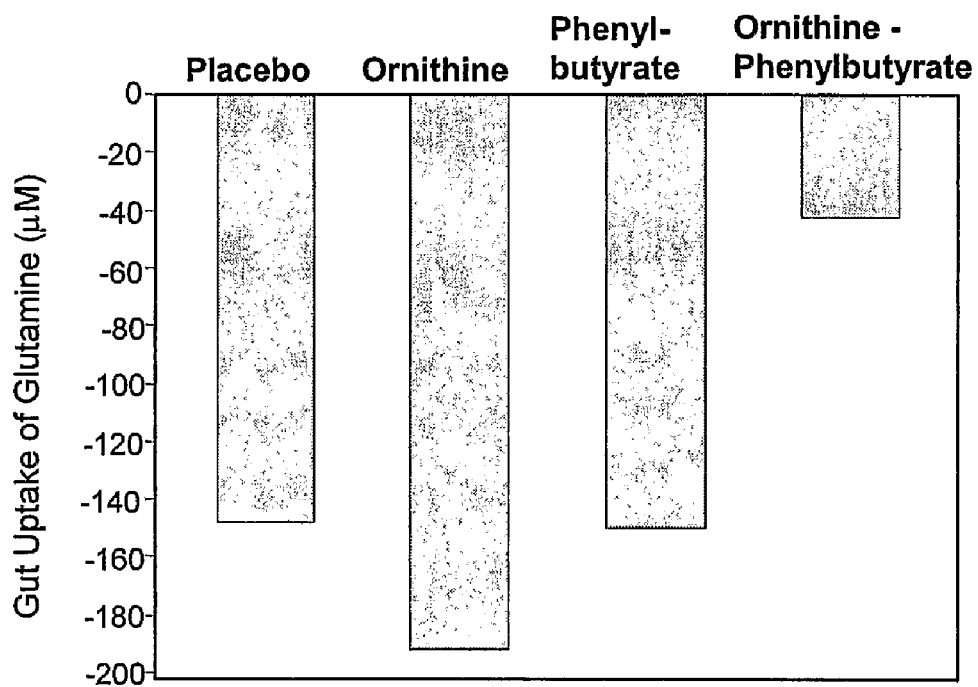
FIG. 26 shows that gut glutamine uptake is enhanced by O, but reduced by OP (thereby reduced generation of ammonia in the gut).

There is a consistent rise in the arterial ammonia concentration with time from devascularisation in the placebo treated animal (FIG. 22), with some muscle production (FIG. 23) and a large amount of ammonia coming from the gut (FIG. 24). This animal shows a modest muscle glutamine release (FIG. 25) and appreciable gut glutamine uptake (FIG. 26).

Figure 22:
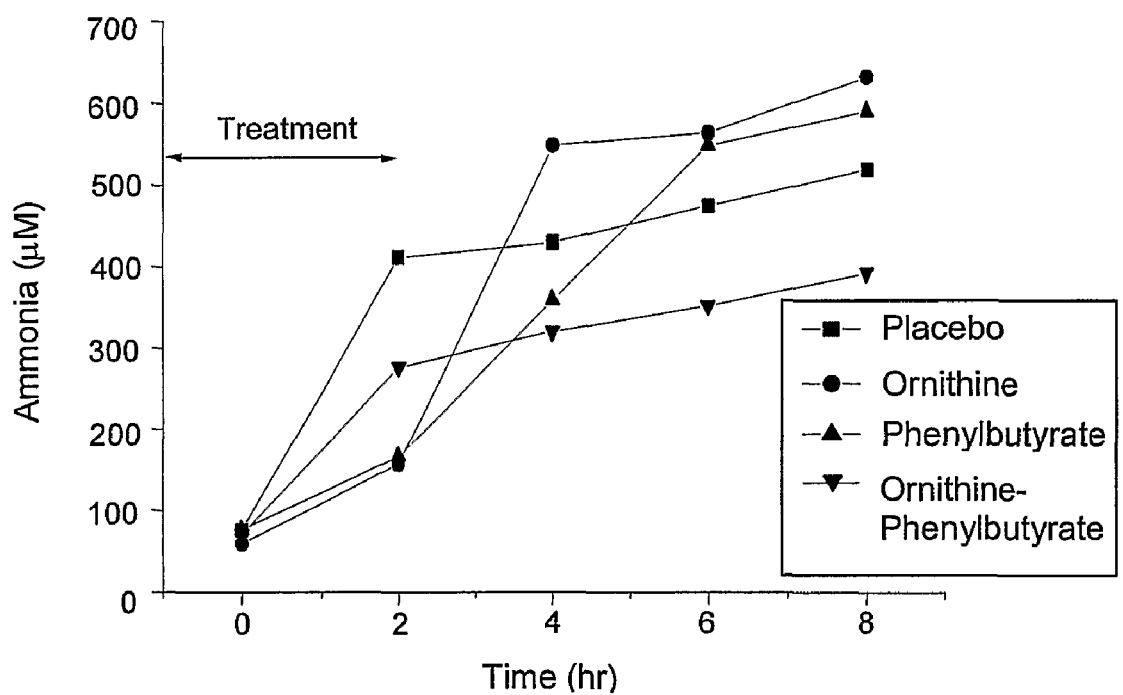
FIG. 22 shows muted arterial ammonia increase in the devascularized pig model of acute liver failure with OP treatment.

In the case of the ornithine alone treated animal, the early ammonia rise is initially blunted, but rises thereafter to be the highest at termination of the experiment (FIG. 22). There is a net uptake of ammonia by the muscle in this animal (FIG. 24), with a comparable amount of glutamine being released from muscle—compared to the placebo treated animal (FIG. 25) with an increased gut uptake of glutamine (FIG. 26).

Phenylbutyrate alone also shows an initial blunting of arterial ammonia levels, which quickly rises to levels comparable with ornithine alone at experiment termination (FIG. 22) with little change in muscle ammonia uptake (FIG. 23), but appreciable gut production of ammonia (FIG. 24). Interestingly, there is a net removal of glutamine by muscle with Phenylbutyrate alone treatment (FIG. 25) with little overt effect on gut glutamine uptake, compared to placebo treated animal (FIG. 26).

The combination of ornithine and Phenylbutyrate has the greatest impact on arterial ammonia levels with an impressive reduction in circulating levels at the end of the experiment compared to all the other animals (FIG. 22). Ammonia is actively removed from the blood by muscle in this animal (FIG. 23) with a greatly reduced gut ammonia production (FIG. 24). It is interesting to note that the muscle glutamine release is increased compared to both the placebo and ornithine alone treated animals (FIG. 25). Despite this increased glutamine production in the muscle the gut glutamine uptake is substantially reduced (FIG. 26).

Figure 27:
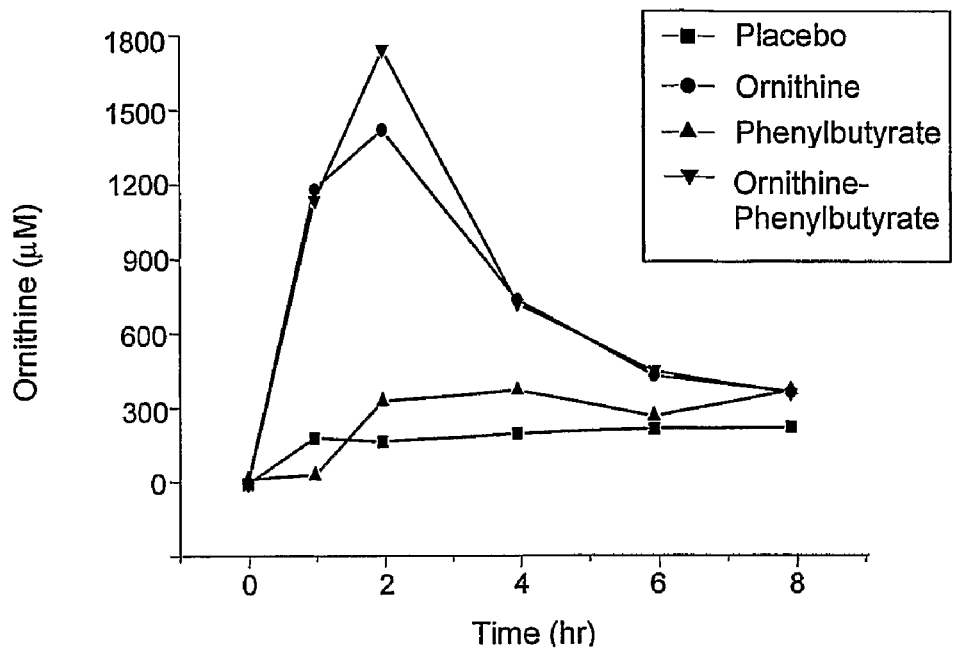
FIG. 27 shows that arterial ornithine levels increase in the two animals (O alone and OP groups) to which it is administered.

A demonstration of increased circulating levels of ornithine in the ornithine treated animals is shown in FIG. 27.

Figure 28:
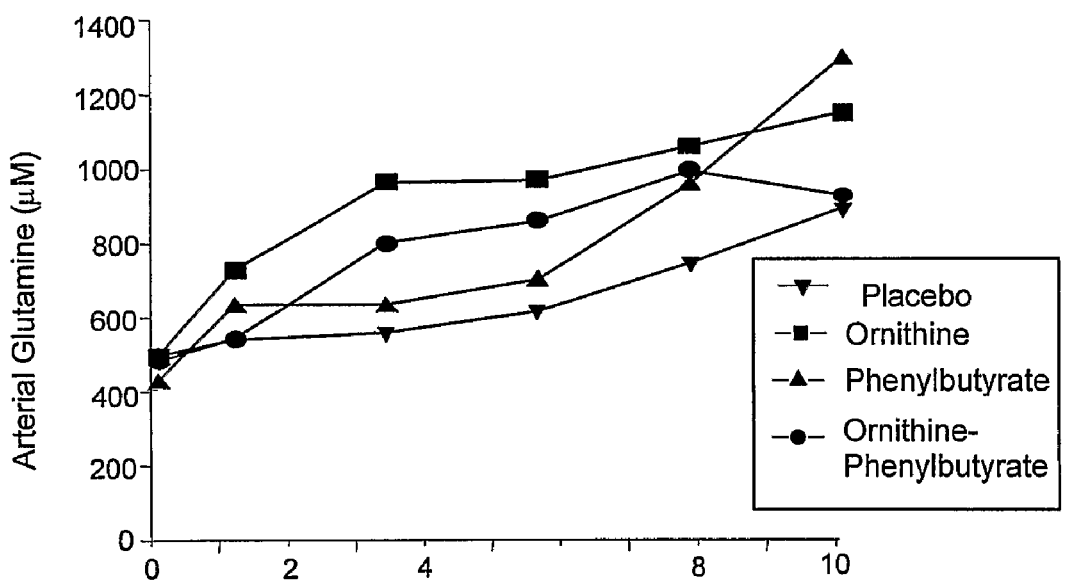
FIG. 28 shows that arterial glutamine levels rise with O, but less so with OP.
Figure 29:
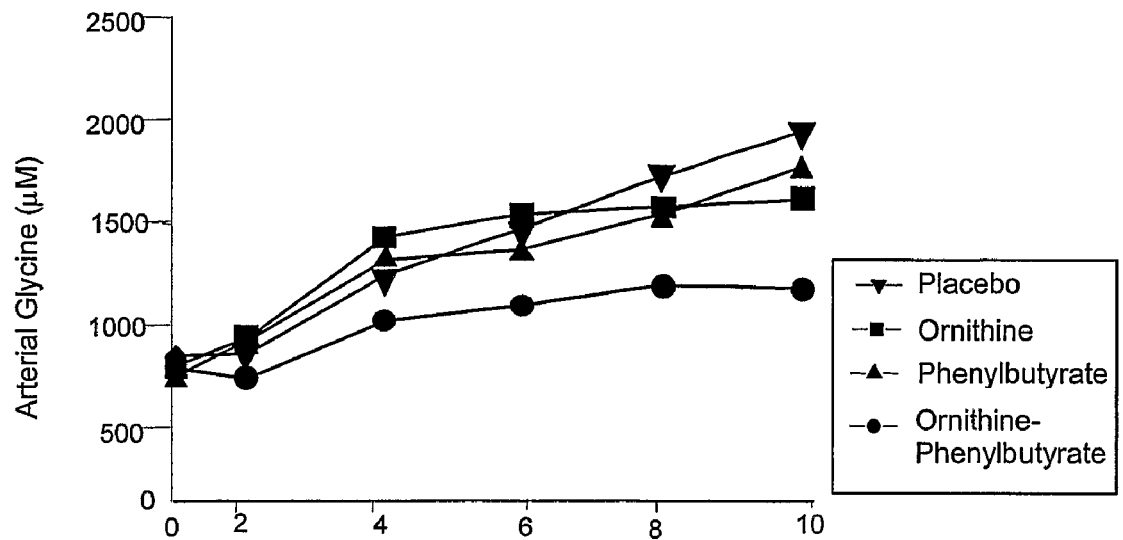
FIG. 29 shows that the combination of OP prevents the increase in the ammoniagenic amino acid glycine.

The impact of the devascularisation and treatment interventions on arterial glutamine are shown in FIG. 28. There is an increase in the circulating level of glutamine in the ornithine treated animal, which is ameliorated by the co-administration of phenylacetate. An interesting finding was the substantial amelioration of the arterial glycine levels that was found in the animal treated with both ornithine and phenylbutyrate (FIG. 29).

Figure 30:
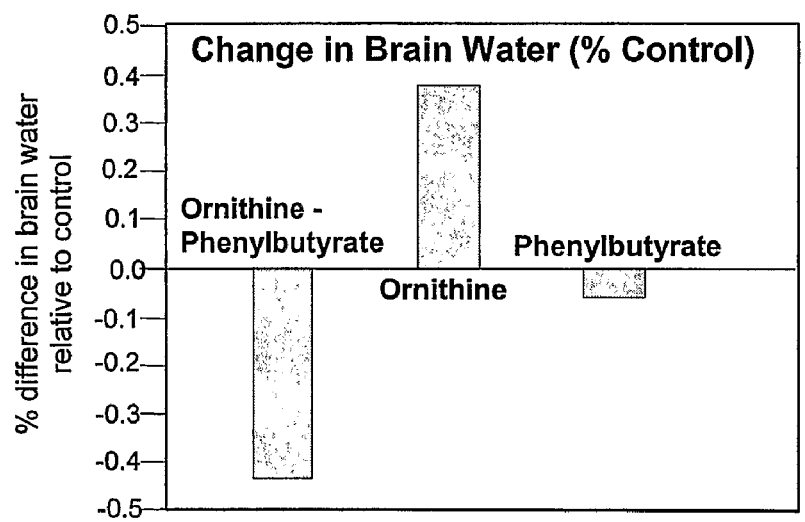
FIG. 30 shows that ornithine alone caused an increase in brain water, phenyl acetate induced a small reduction in brain water, while in combination these agents bring about a substantial reduction in brain water (% control).

At the end of the experiment the frontal cortex of the brain was removed and brain water content measured (FIG. 30).

An independent pathologist reported on the cellular anatomy of the brain in these experimental animals. His report is summarized below.

ALF: Microvessels with perivascular oedema with surrounding vesicles. Neuron with necrotic changes surrounded by vesicles.

ALF+O+P: Microvessels with perivascular oedema with surrounding vesicles (less than from ALF without any treatment). Intracellular edema.

Sham: Brain tissue with minimal ultrastructural changes=normal brain tissue.

CONCLUSIONS

The inventors have found that simulation of some of the symptoms of an acute attack associated with chronic liver disease, such as increasing the concentration of ammonia or simulating a gastrointestinal bleed, results in reduction of neutrophil function and this reduction can be partially reversed by ornithine or isoleucine. Rescue of neutrophil function by both ornithine and isoleucine plays an important role in the prevention of sepsis which is a common precipitating factor in the progression of liver decompensation.

Furthermore, the inventors have found that isoleucine does not affect the rise in concentration of ammonia following a simulated gastrointestinal bleed. Therefore, contrary to the hypothesis that ammonia levels will decrease upon administration of isoleucine because of stimulation of protein synthesis, ammonia levels are unaffected. Thus, use of isoleucine in combination with ornithine, which is known to lower ammonia levels, is particularly advantageous.

Therefore, administration of ornithine and isoleucine prevent the metabolic consequences of a gastrointestinal bleed. Rising ammonia levels are blunted, the deficiency in isoleucine is corrected and neutrophil function is rescued. The combined use of ornithine and isoleucine therefore provides a new treatment for patients following a precipitating event to prevent liver decompensation from occurring.

The inventors have also found that L-ornithine L-aspartate (LOLA), which is used to reduce ammonia in patients with hepatic encephalopathy, does not reverse the effect of ammonia on neutrophil function. Thus, use of ornithine alone is more advantageous than use of LOLA, since ornithine can both reduce ammonia and rescue neutrophil function. Also, the aspartate component of LOLA accumulates in the body. This accumulation of aspartate may actually by harmful to patients since aspartate worsens the effect of ammonia on neutrophil function, further reducing neutrophil function. Accordingly, preventing or delaying the onset of liver decompensation can be achieved using ornithine in combination with isoleucine, preferably in the absence of aspartate.

Furthermore, the inventors have found that treatment of patients with hepatic encephalopathy (HE) with L-ornithine L-aspartate (LOLA) reduces ammonia levels and as a consequence, increases glutamine levels. However, glutamine is only a temporary ammonia buffer as it can recycle and regenerate ammonia in the kidney and the small intestine. Therefore, treatment with LOLA alone can lead to a secondary rise in ammonia levels, further contributing to the pathology of hepatic encephalopathy.

Use of phenylacetate or phenylbutyrate in children with urea cycle disorders reduces the abnormally high levels of glutamine. In contrast, patients suffering from HE have normal levels of glutamine unless, as shown in Example 1, they are being treated with LOLA which reduces levels of ammonia but increases levels of glutamine. Therefore, use of phenylacetate and/or phenylbutyrate allows for the removal of glutamine to prevent the secondary rise in ammonia levels in patients with HE.

Accordingly, an improved treatment for hepatic encephalopathy can be achieved by administration of ornithine in combination with at least one of phenylacetate and phenylbutyrate, preferably in the absence of aspartate.

Our extensive investigations in animal models and also in humans with cirrhosis support the view that the major organ removing ammonia in patients with cirrhosis is the muscle, converting ammonia to glutamine, a reaction in which glutamate is utilised. In liver failure, the enzyme responsible for this reaction, glutamine synthetase is induced and the provision of glutamate would increase ammonia detoxification.

Ornithine, a precursor of glutamate, detoxifies ammonia by transformation to glutamine. However, our preliminary studies have shown that this glutamine, recirculates and regenerates ammonia. Our invention provides a novel method of not only detoxifying ammonia into glutamine but also eliminating the excess glutamine that is generated. Thus, OP reduces ammonia concentration in patients with cirrhosis and hyperammonemia significantly more markedly than either alone. The effect is clearly synergistic rather than additive. In addition, postprandial increase in ammonia is abolished by administration of OP. This may allow for feeding of patients with decompensated cirrhosis with protein-rich diets without the risk of hyperammonemia. The reduction in ammonia was associated with improvement in the mental state. It achieves reduction in ammonia concentration by preventing an increase in glutamine. This is consistent with the hypothesis that Ornithine is driving glutamine production in the muscle (thereby trapping 1 molecule of ammonia) but this glutamine is excreted (possibly as an adduct of phenylacetate) preventing a rise in systemic glutamine, thereby preventing rebound hyperammonemia.

The established wisdom that phenylacetate reduces ammonia in the hyperammonaemic infant presenting with urea cycle disorders is that the ammonia is trapped into glutamine and that the glutamine is shuttled to the kidneys for excretion as the phenylacetateglutamine adduct. These infants present with high ammonia and, importantly, high glutamine. Conversely the cirrhotic patient presents with high ammonia and normal to low glutamine. The pig model described above does not have a raised glutamine and the ammonia levels increase dramatically after the liver is isolated.

Treatment with ornithine alone increases blood glutamine whereas ammonia levels are unaffected. Phenylbutyrate alone marginally increases glutamine and again has insignificant effects on ammonia levels. In dramatic contrast, in this catastrophic model of escalating hyperammonaemia the combination of both ornithine and phenylbutyrate (OP) brings about an appreciable reduction in the circulating ammonia and ameliorates the increase in glutamine seen with ornithine alone. Glycine, an ammonia generating amino acid increased in all the animals, however, the rise in this amino acid was substantially blunted only in the OP treated animal, suggesting additional benefit for this form of intervention. An established consequence of elevated ammonia is brain swelling as water content of the brain increases. The brain from ornithine alone treated pig shows considerable increase in water content while the ornithine and phenylbutyrate combined reduces brain water content. Histologically, there is less apparent injury in the microstructure of the brain of the ornithine and phenylbutyrate combined treatment animal compared to the placebo treated animal.

The invention claimed is:

1. A method of treating hepatic encephalopathy, comprising administering to a patient in need thereof a single pharmaceutical composition comprising ornithine and at least one of phenylacetate or phenylbutyrate, wherein the dosage of ornithine administered is from 1 g to 50 g and the dosage of phenylacetate or phenylbutyrate administered is from 1 g to 50 g and the weight ratio of ornithine to phenylacetate or phenylbutyrate in the composition is from 2:1 to 1:2 and the amounts administered are effective to reduce, or attenuate an increase in, blood ammonia in said patient, wherein the patient has chronic liver disease or acute liver failure, wherein the pharmaceutical composition comprises substantially no other amino acid.

2. The method of claim 1, wherein the administration ameliorates one or more symptoms of the hepatic encephalopathy.

3. The method of claim 1, wherein the pharmaceutical composition comprises substantially no aspartate.

4. The method of claim 1, wherein the pharmaceutical composition comprises no aspartate.

5. The method of claim 1, wherein the pharmaceutical composition comprises no other amino acid.

6. The method of claim 1, wherein the pharmaceutical composition consists essentially of ornithine and at least one of phenylacetate and phenylbutyrate.

7. The method of claim 1, wherein from 0.02 g/kg to 1.25 g/kg of ornithine and from 0.02 g/kg to 1.25 g/kg of phenylacetate or phenylbutyrate is administered to said patient.

8. The method of claim 1, wherein from 0.1 g/kg to 0.5 g/kg of ornithine and from 0.1 g/kg to 0.5 g/kg of phenylacetate or phenylbutyrate is administered to said patient.

9. The method of claim 1, wherein from 5 g to 30 g of ornithine and from 5 g to 30 g of at least one of phenylacetate or phenylbutyrate are administered to said patient.

10. A method according to claim 1 wherein said ornithine is present as a free monomeric amino acid or physiologically acceptable salt.

11. A method according to claim 1 wherein the at least one of phenylacetate and phenylbutyrate is present as sodium phenylacetate or sodium phenylbutyrate.

12. A method according to claim 1 wherein said administration is intravenous, intraperitoneal, intragastric, intravascular or oral administration.

13. The method of claim 1, wherein the effective amount of ornithine and at least one of phenylacetate and phenylbutyrate is administered to a patient having chronic liver disease.

14. The method of claim 13, wherein the effective amount of ornithine and at least one of phenylacetate and phenylbutyrate is administered to a patient having liver cirrhosis.

15. The method of claim 1, wherein the effective amount of ornithine and at least one of phenylacetate and phenylbutyrate is administered to a patient having acute liver failure.

16. A method of reducing the likelihood of the onset of, or delaying the onset of, hepatic encephalopathy, comprising administering to a patient at risk thereof a single pharmaceutical composition comprising ornithine and at least one of phenylacetate or phenylbutyrate, wherein the dosage of ornithine administered is from 1 g to 50 g and the dosage of phenylacetate or phenylbutyrate administered is from 1 g to 50 g and the weight ratio of ornithine to phenylacetate or phenylbutyrate in the composition is from 2:1 to 1:2 and the amounts administered are effective to reduce, or attenuate an increase in, blood ammonia in said patient, wherein the patient has chronic liver disease or acute liver failure, wherein the pharmaceutical composition comprises substantially no other amino acid.

17. A method of claim 16, wherein said ornithine is present as a free monomeric amino acid or physiologically acceptable salt.

18. A method of claim 16, wherein the at least one of phenylacetate and phenylbutyrate is present as sodium phenylacetate or sodium phenylbutyrate.

19. A method of claim 16, wherein said administration is intravenous, intraperitoneal, intragastric, intravascular or oral administration.

20. The method of claim 16, wherein the effective amount of ornithine and at least one of phenylacetate and phenylbutyrate is administered to a patient having chronic liver disease.

21. The method of claim 20, wherein the effective amount of ornithine and at least one of phenylacetate and phenylbutyrate is administered to a patient having liver cirrhosis.

22. The method of claim 16, wherein the effective amount of ornithine and at least one of phenylacetate and phenylbutyrate is administered to a patient having acute liver failure.

23. The method of claim 16, wherein the pharmaceutical composition comprises no aspartate.

24. The method of claim 16, wherein the pharmaceutical composition comprises substantially no aspartate.

25. The method of claim 16, wherein the pharmaceutical composition comprises no other amino acid.

26. The method of claim 16, wherein the pharmaceutical composition consists essentially of ornithine and at least one of phenylacetate and phenylbutyrate.

27. The method of claim 16, wherein from 0.02 g/kg to 1.25 g/kg of ornithine and from 0.02 g/kg to 1.25 g/kg of phenylacetate or phenylbutyrate is administered to said patient.

28. The method of claim 16, wherein from 0.1 g/kg to 0.5 g/kg of ornithine and from 0.1 g/kg to 0.5 g/kg of phenylacetate or phenylbutyrate is administered to said patient.

29. The method of claim 16, wherein from 5 g to 30 g of ornithine and from 5 g to 30 g of at least one of phenylacetate or phenylbutyrate are administered to said patient.

30. A method according to claim 16 wherein the patient has had or is suspected of having had a precipitating event.

31. A method according to claim 30, wherein said precipitating event is gastrointestinal bleeding, infection, portal vein thrombosis or dehydration.

32. A method according to claim 30, wherein the ornithine and at least one of phenylacetate and phenylbutyrate is administered within 6 hours of a symptom(s) of said precipitating event or suspected precipitating event having been detected.

33. The method of claim 16, wherein the administration reduces the likelihood of onset of hepatic encephalopathy.

* * * * *